United States Patent [19]
Marasco et al.

[11] Patent Number: 6,004,940
[45] Date of Patent: *Dec. 21, 1999

[54] INTRACELLULAR TARGETING OF ENDOGENOUS PROTEINS

[75] Inventors: Wayne A. Marasco, Wellesley; Jennifer Richardson, Cambridge, both of Mass.

[73] Assignee: Dana-Farber Cancer Institute, Inc., Boston, Mass.

[*] Notice: This patent is subject to a terminal disclaimer.

[21] Appl. No.: 08/350,215

[22] Filed: Dec. 6, 1994

Related U.S. Application Data

[63] Continuation of application No. 08/045,274, Mar. 31, 1993, abandoned, which is a continuation-in-part of application No. 07/916,939, Jul. 17, 1992, abandoned.

[51] Int. Cl.[6] .................................................. A61K 48/00
[52] U.S. Cl. ........................ 514/44; 435/320.1; 536/23.1; 536/23.53
[58] Field of Search .............................. 514/44; 435/69.7, 435/240.2, 320.1; 935/23, 34, 47, 70; 530/387.1; 536/23.1, 23.53

[56] References Cited

FOREIGN PATENT DOCUMENTS

WO94/02610  2/1994  WIPO ............................ C12N 15/13

OTHER PUBLICATIONS

Baringga; M. Science 1994 vol. 266, p. 1326.
Marshall. E Science 1995 vol. 269, pp. 1050–1055.
Crystal R. Science 1995 vol. 270 .p. 404–410.
Orkin et al. 1995. Report and Recommendations of the Panel to Assess the NIH investment in research on Gene Therapy.
Beerli et al., "Autocrine inhibition of the epidermal growth factor receptor by intracelular expression of a single–chain antibody", Biochem. Biophys. Res. Commun. 204(2): 666–672, Oct. 1994.
Biocca et al., "Intracellular immunization: Expression of antibody domains in the cytoplasm and in the nucleus of mammalian cells", Cytotechnol. 5: S49–50, 1991.
Werge et al., "Intracellular immunization: Cloning and intracellular expression of a monoclonal antibody to the p12ras protein", FEBS Letts 274: 193–198, Nov. 1990.
Palker, "Human T–cell lymphotrophic viruses: Review and prospects for antiviral therapy", Antiviral Chem. Chemother., 3(3): 127–139, 1992.
Spence et al., "Affinity purification and characterization of anti–Tac (Fv)–C3–PE38KDEL: A highly potent cytotoxic agent specific to cells bearing IL–2 receptors", Bioconjugate Chem. 4: 63–68, 1993.
T. Werge, et al., FEBS, 274: 193–198 (1990).
Chaudhary et al., Proc. Natl. Acad. Sci., 87:308–312.
H. Siomi et al., Cell, 55:197–209 (1988).
Schultz et al., Biochem. Biophys. Res. Commun., 146:1234–1239 (1987).
Posner. Journal of Immunology, 146 (12):4325–4332 (1991).
Brake, et al., J.Virol, 64 (2):962–965 (1990).
Spence, et al., Bioconjugate Chem., 4(1):63–68 (1993).
Kreitman, et al.,Bioconjugate Chem., 4(2):112–120 (1993).
Norley, et al., "Vaccinations against HIV", Immunobiol, vol. 184, pp. 193–207 (1992).
Faraji–Shadan, et al., "A Positive Approach for Gene Therapy Against Human Immunodeficiency Virus (HIV)" Medical Hypothesis, vol. 32 pp. 81–84 (1990).
Biocca et al., "Intracellular Immunization: Expression of Antibody Domains in the Cytoplasm and in the Nucleus of Mammalian Cells", Cytotechnol. 5: S49–50, (1991).

*Primary Examiner*—Nancy Degen
*Assistant Examiner*—Irem Yucel
*Attorney, Agent, or Firm*—Ronald I. Eisenstein; David S. Resnick

[57] ABSTRACT

The present invention relates to a method by which one can target an undesired target molecule or target antigen, preferably an endogenous protein. The method comprises the intracellular expression of an antibody capable of binding to the target. A DNA sequence is delivered to a cell, the DNA sequence contains a sufficient number of nucleotides coding for the portion of an antibody capable of binding to the target operably linked to a promoter that will permit expression of the antibody in the cell(s) of interest. The antibody is then expressed intracellularly and binds to the target, thereby disrupting the target from its normal actions.

32 Claims, 6 Drawing Sheets

INTRACELLULAR TARGETING OF ENDOGENOUS PROTEINS

The present application is a continuation of U.S. Ser. No. 08/045,274 filed Mar. 31, 1993, now abandoned, which was a continuation-in-part of U.S. Ser. No. 07/916,939 filed Jul. 17, 1992, now abandoned.

The present invention is directed to a method for the intracellular binding of target molecules, preferably proteins, more preferably endogenous transmembrane proteins such as components of cellular receptors. More specifically, this method involves the intracellular expression and subsequent use of antibodies that specifically target a desired molecule.

BACKGROUND OF THE INVENTION

The presence of molecules in or on cell are responsible for a variety of effects. For example, various abnormalities appear to be the result of the undesired expression of a particular protein. Thus, many tumors are believed to be the result of the overexpression of cellular oncogenes, such as neu, myc, abl, etc. Other malignancies are believed to be the result of expression of an altered receptor. Still other illnesses, such as certain leukaemias, result from the overexpression of cellular receptors which leads to the unregulated growth of these cells, as in B and T cell leukaemias. Other malignancies are associated with the expression of certain proteins.

Interleukin-2 (IL-2), for example, is a cytokine of central importance to the immune system, stimulating growth and effector functions in a variety of cell types including T lymphocytes, B lymphocytes, monocytes, LAK and natural killer cells [Smith, K. A. *Science* 240:1169–1176 (1988); Waldmann, T. A., et al. *J. Exp. Med.* 160:1450–1456 (1984); Seigel, J. P., et al., *Science* 238:75–78 (1987); Minami, Y., et al., *Ann. Rev. Immunol.* 11:245–267 (1993)]. The response of peripheral blood T cells to (physiological concentrations of) IL-2 is a two stage, antigen-driven process. Antigenic stimulation of resting T cells first induces the appearance of high affinity IL-2 receptors and the production of IL-2 [Meuer, S. C., et al. *Proc. Natl. Acad. Sci. USA* 81:1509–1513 (1984); Cantrell, D. A. & Smith, K. A. *j. Exp. Med.* 158:1895–1911 (1983)]. Interaction of IL-2 with the high affinity receptor then initiates a cascade of signalling events [Minami, Y., *Ann. Rev. Immunol.* 11, supra; Johnston, J. A., et al., *Nature* 370:151–153 (1994)] which culminates in cell proliferation [Meuer, S. C., et al. *Proc. Natl. Acad. Sci. USA* 81:1509–1513 (1984); Smith, K. A. & Cantrell, D. A. *Proc. Natl. Acad. Sci. USA* 82:864–868 (1985)].

The high affinity IL-2 receptor is a heterotrimer composed of α, β and γ chains. [Minami, Y., *Ann. Rev. Immunol.* 11, supra; Takeshita, I., et al. *Science* 257:379–382 (1992)]. The β and γ chains (IL-2Rβ and IL-2Rγ) are constitutively expressed on resting T cells and together form a receptor of intermediate affinity [Takeshita, I., et al. *Science* 257:379–382 (1992); Lê thi Bich-Thuy, Dukovitch, M., et al. *J. Immunol.* 139:1550–1556 (1987)]. Expression of the 55 kD α chain (hereinafter "IL-2Rα" or "Tac") and hence the high affinity receptor, occurs only transiently following engagement of the T cell receptor and is a key point of regulation in the T cell response to antigen [Smith, K. A., et al., *Proc. Natl. Acad. Sci. USA* 82, supra].

The overexpression of IL-2Rα results in a variety of T and B cell leukaemias, most notably in HTVL-1 associated adult T cell leukaemia [Waldman, T. A., et al., *Ann. Intern. Med.* 116:148–160 (1992)], where it is strongly implicated in the deregulated growth of these cells. The constitutive upregulation of IL-2Rα in certain T and B cell leukaemias and its association with T cell activation makes this receptor chain a natural target for suppressive immunotherapy. Therefore, the availability of an effective tool for inhibiting the expression of IL-2Rα would provide a powerful reagent for gene therapy.

Therapeutic strategies to combat conditions caused by undesired expression of a protein have included the development of drugs to target the undesired proteins, means of intercellular blocking of such proteins, for example, the use of an antibody to the protein on the cell surface, and the use of drugs which will selectively kill cells expressing the undesired proteins.

For example, therapeutic strategies based on the blockade of the high affinity receptor by monoclonal antibodies (mAbs) directed against IL-2Rα have been used to try to dampen a variety of other undesirable T cell-mediated reactions including allograft rejection, graft versus host disease and some forms of autoimmunity [Strom, T. B., et al., *Immunological Reviews* 129:131–163 (1992)]. Humanized mAbs against IL-2Rα and immunotoxins such as IL-2 fused to the catalytic domain of pseudomonas exotoxin (IL-2 PE40) have also been used to selectively eradicate leukaemic or otherwise harmful T cells bearing the high affinity IL-2 receptor [Waldman, T. A., et al., *Ann. Intern. Med.* 116:148–160 (1992)]. However, the use of such immunotoxins and antibodies, particularly the repeated use of such antigenic molecules can elicit an immune reaction rendering their repeated use problematic.

Modem molecular techniques which inhibit the expression of specific genes provide methods for the manipulation of individual genes and cellular pathways. For example, techniques using antisense RNA, ribozymes, dominant negative mutants and targeted gene disruption have all been successfully used to inhibit the expression or function of specific genes. [Neckers, L. & Whitesell, L., *Am. J. Physiol.* 245:11–12 (1993); Erickson, R. P., *Dev. Gene.* 14:251–257 (1993); Bratty, J., et al., *Biochimica et Biophysica Acta.* 1261:345–359 (1993); Schaap, D., et al., *J. Biol. Chem.* 268:20232–20236 (1993); Capecchi, M. R., Sci. Am. 270-52-58 (1994)]. However, these methods have certain limitations. The dominant negative mutant approach, for example, requires the availability of a functionally inactive mutant which acts in a dominant manner to suppress the activity of the wild type protein. Procedures using antisense RNA produce inhibitory effects that are frequently incomplete or short lived [Neckers, L. & Whitesell, L., *Am. J. Physiol.* 245:11–12 (1993); Erickson, R. P., *Dev. Gene.* 14:251–257 (1993); Nellen, W., et al., *TIBS* 18:419–423 (1993)]. A major impediment to the development of effective gene inhibition protocols using antisense RNA or ribozymes is the inability to achieve a high level of expression of the inhibitor encoding DNA template in the transformed cells. This may also be a potential problem with using dominant negative mutants because of the competitive nature of the inhibition. Additionally, the targeted gene disruption technique is limited because this method cannot readily be applied to cells en masse.

It would, therefore, be desirable to have a method which can be used to achieve a high level of expression of an inhibitor to the desired molecule, specifically to IL-2 receptor proteins.

It would be desirable to have a method which can specifically target these proteins and which has wide applicability.

In U.S. patent applications Ser. Nos. 07/916,939 and 08/045,274 and PCT/US93/06735 (which is incorporated herein by reference) we discussed a method by which one can target a target molecule by the intracellular expression of antibodies ("intrabodies") for example, by targeting to specific proteins such as viral proteins, preventing their transport to the cell surface [Marasco, W. A., et al., *Proc. Natl. Acad. Sci. USA* 90:7889–7893 (1993)].

It would be desirable to have a method which does not introduce cytotoxic chemicals into a cell.

It would be desirable to have a method which provides a ready means of targeting undesired proteins.

SUMMARY OF THE INVENTION

We have discovered a method by which one can target an undesired molecule (sometimes referred to as a "target", "target molecule" or "target antigen"). We describe herein its use against endogenous molecules, preferably a protein, more preferably a protein that traverses the cellular membrane such as an endogenous transmembrane protein, a secreted protein, an integral membrane protein, a gp1-anchored protein, still more preferably a transmembrane protein such as a cellular receptor such as the IL-2 receptor. This method comprises the intracellular expression of an antibody capable of binding to the target. A DNA sequence (referred to as an "antibody cassette"), containing a sufficient number of nucleotides coding for the portion of an antibody capable of binding to the target operably linked to a promoter that will permit expression of the antibody in the cell(s) of interest, is delivered to a cell. Thereafter, the antibody is expressed intracellularly and binds to the target, thereby disrupting the target from its normal action. This antibody is sometimes referred to as an "intrabody". In one preferred embodiment, the "intrabody gene" (antibody) of the antibody cassette would utilize a cDNA, encoding heavy chain variable ($V_H$) and light chain variable ($V_L$) domains of an antibody which can be connected at the DNA level by an appropriate oligonucleotide as a bridge of the two variable domains, which on translation, form a single peptide (referred to as a single chain variable fragment, "sFv") capable of binding to a target such as a protein. The intrabody gene preferably does not encode an operable secretory sequence and thus the expressed antibody remains within the cell. In certain embodiments, a nucleotide sequence encoding an intracellular localization leader is also used.

One preferred cell target includes cellular receptors or their components. More preferably, the target is a cellular receptor which is expressed in high number on cells showing an undesired characteristic. For example, the high affinity IL-2 receptor, e.g., one can target part of the IL-2 receptor, preferably IL-2Rα, a component of the high affinity interleukin-2 receptor.

The capacity to disrupt the expression of specific IL-2 receptor chains in cells such as primary lymphocytes and established cell lines can have both therapeutic value and utility for drug screening. For example, an anti-IL-2 antibody (referred to as a Tac antibody) can be used. Preferably, one uses a single chain antibody (sFv). More preferably, one uses a Tac antibody with a specific cellular localization sequence. For example, one preferred cellular location to target is the endoplasmic reticulum (ER). A preferred localization sequence is the KDEL sequence. Preferred single-chain intrabodies of this invention, hereinafter referred to as "sFvTac", "sFvTacKDEL", can be used to down regulate IL-2Rα. No toxicity is associated with intracellular expression of the IL-2Rα intrabodies in cells that do not require IL-2 Rα for viability, and the transport of other plasma membrane proteins is unaffected. The intrabodies of this invention are efficient and specific and are useful in regulating receptors, such as IL-2 receptors. The stable introduction of genes encoding single-chain intrabodies, therefore, provides a powerful alternative to antisense RNA, ribozymes and other methods of gene inactivation.

BRIEF DESCRIPTION OF THE DRAWINGS

FIGS. 3A and B, show parental Jurkat cell line before (FIG. 3A) and after (FIG. 3B) PHA/PMA stimulation. FIGS. 3C and D show PHA/PMA stimulated clones expressing sFvTacKDEL (FIG. 3C) or sFvTac (FIG. 3D).

DETAILED DESCRIPTION OF THE INVENTION

Figure 1:
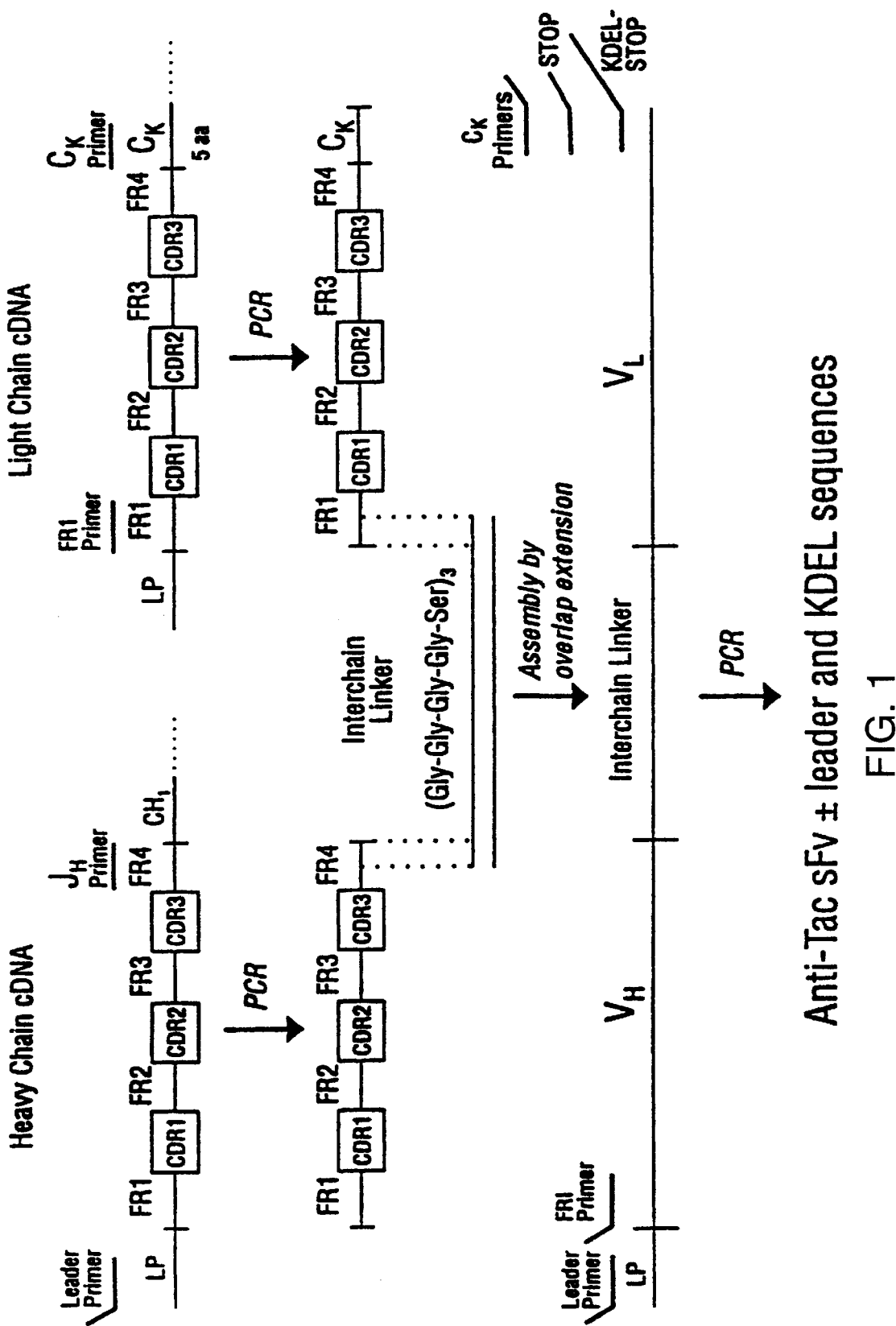
FIG. 1 is a schematic diagram showing the construction of certain sFvTac genes. The individual heavy and light chain variable regions and interchain linker are each amplified by PCR and the sFv gene then assembled by overlap extension. The leader peptide (LP), framework regions (FR) and complementarity-determining regions (CDR) are indicated.

The present invention is directed to a method of targeting a particular molecule ("target molecule"), preferably an endogenous protein the expression of which is undesired at that time. This method comprises the intracellular expression of an antibody (intrabody) which is capable of binding to a specific target (e.g. a "target protein"), wherein the antibody preferably does not contain sequences coding for its secretion. Such antibodies will bind the target intracellularly. As used herein, the term antibody refers to at least that portion of an immunoglobulin capable of selectively binding to a target such as a protein. The antibody is expressed from a DNA sequence which contains a sufficient number of nucleotides coding for the portion of an antibody capable of binding to the target, referred to herein as the "antibody (or intrabody) gene". The gene is operably linked to a promoter that will permit expression of the antibody in the cell(s) of interest. Promoters are well known in the art and can readily be selected depending on the cell type desired to be targeted. Furthermore, the use of inducible promoters, which are also well known in the art, in some embodiments are preferred, such as when the function of a target protein is a result of its overexpression. By "turning the promoter on" one can selectively obtain the expression of the antibody.

The entire sequence of intrabody gene and promoter is described herein as an "antibody cassette". The cassette is delivered to the cell by any of a number of means, such as those described below, which permit intracellular delivery of a gene. The expressed single chain intrabody can then bind to the target antigen. This permits a wide variety of useful applications.

Almost any kind of biologic molecule can serve as a target antigen, for example, intermediate metabolites, sugars, lipids, autacoids, and hormones as well as macromolecules such as complex carbohydrates, phospholipids, nucleic acids such as RNA and DNA, and proteins. The skilled artisan can generate antibodies that will specifically bind to both small molecules and macromolecules. For example, with small molecules one commonly attaches the small molecule (sometimes referred to as a hapten) to a macromolecule (sometimes referred to as a carrier) before immunization. The hapten-carrier complex acts as an immunogen. Antibodies that will specifically bind to a wide range of targets are known. The preferred target molecules include proteins, RNA, DNA and haptens. More preferably, the targets are proteins, RNA and DNA. Still more preferably, the target is a protein. More preferably, it is an endogenous protein. Even more preferably, the protein is a protein that traverses a cellular membrane, such as a transmembrane protein, an integral membrane protein, a secreted protein, or a gp1-anchored protein, and still more preferably a transmembrane protein. In this application, a particularly preferred transmembrane protein is a member of a receptor. A preferred receptor is the IL-2 receptor. The high affinity IL-2 receptor is the more preferred receptor. A preferred target component of this receptor is the α chain, IL-2Rα.

By intracellular binding to target proteins such as IL-2 Rα, oncogenes, etc. it is possible to disrupt the normal functioning of such proteins reducing or avoiding the disruptive effect of the protein. Overexpression of a number of oncogenes has been reported to be associated with malignant cellular transformation. For example, amplification of myc has been reported in COLO 320 colon carcinoma cell cultures, the SKBR3 breast carcinoma cell line and in lung carcinoma cell lines. Amplification of N-myc has been reported in neuroblastoma cell lines and retinoblastoma. Amplification of c-abl, c-myb, and other oncogenes have also been reported to be associated with malignant transformation. See, chapter 12 "Human Oncogenes" pp 487–543, *RNA Tumor Viruses, Molecular Biology of Tumor Viruses*, 2nd Ed., Weiss, R. et al., Ed. (Cold Spring Harbor Laboratory (1985)).

High levels of various oncogenes has also been reported to effect the risk of recurrence of the tumor. For example, a correlation between the level of neu/c-erbB-2 and the cause and course of human breast cancer has been reported. See, Paterson, M. C., et al., *Cancer Research* 51:556–567 (1991); high levels of myc, int-2 and hst-1 have also been associated with breast cancer. Similarly, elevated levels of the receptor for EGF, EGF-R have been shown to be associated with breast cancer. Grimaux, M., et al., *Int. J. Cancer* 45:255–262 (1990). The overexpression of these and other oncogenes have also been reported as being associated with other cancers.

Many oncogenes show some homology to genes involved in cell growth. For example, see the table below.

TABLE 1[1]

| CATEGORY | ONCOGENE | HOMOLOGOUS CELLULAR GENE |
|---|---|---|
| Growth Factors | sis | PDGF-/2 |
|  | int-2 | FGF-like |
| Transmembrane growth factors | erbB | EGF receptor |
|  | neu (erbB-2, HER-2) |  |
|  | fms | M-CSF receptor |
|  | ros, kit, and others |  |
| Membrane-associated tyrosine kinases | abl |  |
| Membrane associated guanine nucleotide binding proteins | src family[2] fes, fps[3] K-, N- and H-ras |  |
| Cytoplasmic serine-threonine kinases | raf/mil mos |  |
| Cytoplasmid hormone receptors | erbA | Thyroid hormone receptor |
| Nuclear factors | c-myc, N-myc, L-myc, fos, jun, myb, ets, ski, and others |  |
| Antioncogenes | RB |  |
| Others | bcl-2 bcl-1 int-1 |  |

[1]Adapted from Druker, B. J., et al., N. Eng. J. of Mol. 321:1383–1392 (1989). PDGF denotes platelet-derived growth factor, FGF fibroblast growth factor, EGF epidermal growth factor, and M-CSF mononuclear-phagocyte growth factor.
[2]The family includes src, fgr, yes, lck, hck, fyn, lyn, and tkl.
[3]The subcellular location of these oncongene products is uncertain.

Antibodies to most of these oncogenes have been reported. In addition, to overexpression of oncogenes (sometimes referred to as oncs), some oncogenes undergo a mutation from a proto-onc (normal gene for normal protein) to an onc (gene whose protein can cause malignant transformation) which appears to result in malignant transformation of cells. For example, point mutations of the ras gene at the codons for the ras p21 at residue positions 12, 13 and 61 have resulted in mutant ras p21 proteins which are associated with various cancers. Antibodies specific to many of these ras mutants are known.

This method can be used in a variety of methods. For example, binding to a protein that has a significant external domain can hinder the effect of the protein.

In another embodiment, by binding to a dysfunctional receptor protein, one can block the undesired interactions that can result in cellular dysfunction such as malignant transformation.

For example, many proteins, such as surface receptors, transmembrane proteins, etc. are processed through the endoplasmic reticulum (sometimes referred to as ER)-Golgi apparatus. Examples of such proteins include neu, IL-2 subunits, e.g. IL-2Rα. By using antibodies that can be delivered to such a region of the cell and be specific for a particular protein, one can disrupt the function of such protein without disrupting other cellular functions. For example, the PDGF-/2 and FGF-like factors produced by sis and int-2 pass through the ER. These factors are involved in many cancers. Thus, in addition to targeting the receptor, one can target the growth factors by using antibodies to them.

Growth factors are also expressed by many other malignant cells such as from carcinoid syndrome tumors and these would be another target.

One can also use this method to disrupt a function that is undesirable at a particular time. For example, the MHC class I and class II molecules are important in the immune systems recognition of antigens. [Teyton, L., et al., *The New Biologist* 4:441–447 (1992); Cox, J. H., et al., *Science* 247:715–718 (1990); Peters, P. J., et al., *Nature* 349:669–676 (1991); Hackett, *Nature* 349:655–656 (1991)]. However, such immune recognition, particularly from MHC class I molecules can cause problems such as in organ transplants. [Schreiner, G. F., et al., *Science* 240:1032–1033 (1988)]. Thus, by targeting class I molecules with organ transplants you can down regulate the host immune response. These molecules can preferably be targeted at different points in their processing pathway. Preferably, one would use an inducible promoter for the antibody gene.

Thus, by taking into account the particular target many variations of this method can be designed by the skilled artisan.

Numerous sites can be targeted. For example, the endoplasmic reticulum-Golgi apparatus is one preferred site because processing of many proteins occurs there. Targeting the cytoplasmic side of a membrane receptor is another site. It is through the cytoplasmic tail that signal transduction occurs. [Luttrell, L. M. et al., Science 259:1453–1457 (1993); Epstein, R. J., et al., *Proc. Natl. Acad. Sci USA* 89:10435–10439 (1992)]. For example, using the neu/erbB-2 receptor or G protein receptor one can target the loop or cytoplasmic tail thereby preventing such signal transduction. For example, one preferably uses antibodies to activated receptors such as to phosphorylated amino acids. Thus, the pool of target receptors can be reduced.

The antibodies will bind specifically to the target, e.g. a protein, and can thus effectively compete with other molecules that will also form complexes with the protein. To insure that the antibodies of the present invention can compete successfully with other molecules, they must retain at least about 75% of the binding effectiveness of the complete antibody to that target, i.e. having constant as well as variable regions. More preferably, it has at least 85% of the binding effectiveness of the complete antibody. Still more preferably, it has at least 90% of the binding effectiveness of the complete antibody. Even more preferably, it has at least 95% of the binding effectiveness.

As will be discussed in greater detail below, intracellular expression of an antibody to its target, for example, the antibody to the IL-2Rα protein, results in an antibody that binds the target in the cell and can prevent further processing of the IL-2 receptor.

In a preferred embodiment a localization sequence is used, preferably an ER-localized single-chain intrabody to inhibit the cell surface expression of, for example, IL-2Rα. IL-2Rα is an essential component of the high affinity IL-2 receptor. [Smith, K. A. *Science* 240:1169–1176 (1988); Minami, Y., et al., *Ann. Rev. Immunol.* 11:245–267 (1993)]. This inducible receptor chain regulates cell activation and is constitutively upregulated in a variety of T and B cell leukaemias. [Waldman, T. A., et al., *Ann. Intern. Med.* 116:148–160 (1992)]. Inactivation of IL-2Rα, can be useful in decreasing the number of high affinity IL-2 receptors and therefore in regulating cell proliferation. For example, construction of a gene encoding an antibody, preferably, a single-chain variable region fragment ("sFv") of the anti-Tac monoclonal antibody, which recognizes IL-2Rα such as one with a signal peptide and a C-terminal ER retention signal. Such an intrabody, called "sFvTac KDEL", is used to target the desired cells. Intracellular expression of the single-chain intrabody can completely abrogate cell surface expression of IL-2Rα in PMA-stimulated Jurkat cells. Furthermore, this result is achieved without disrupting other cellular functions.

The target molecules can be present in a wide range of hosts, including animals and plants. Preferably, the host is an animal and more preferably, the species is one that has industrial importance such as fowl, pigs, cattle, cows, sheep, etc. Most preferably, the species is a human.

Although antibodies have the ability to recognize an almost limitless number of foreign molecules, in nature, antibodies recognize structures exterior to the cell. [Winter, G., et al., *Nature* 349:293 (1991)]. Once synthesized, antibodies are secreted into the surrounding fluid or remain bound to the outer cell membrane [Klein, *Immunology*, Blackwell Scientific Publications, Cambridge, Mass. 1990]. We have found a means, however, to express antibodies which retain the ability to specifically bind to a target intracellularly. Thus, specificity for a particular target can be obtained by using the immune system, itself. One uses the target or an antigenic portion thereof or a hapten-carrier complex to generate an antibody. This can be accomplished by standard techniques.

For example, the antigen binding or variable region is formed by the interaction of the variable heavy ($V_H$) and variable light ($V_L$) domains at the amino termini of the chains. The smallest fragment containing a complete binding site is referred to as Fv and is a heterodimer of the $V_H$ and $V_L$ domains. However, it is possible to obtain binding without a complete binding site. For example, one can obtain antigen binding activity using only a heavy chain binding domain (dAbs, also referred to as single domain antibodies). As aforesaid, in the present invention, one can use a gene coding for such an antibody fragment as long as it retains sufficient binding ability compared to the parent antibody. Preferably, one uses at least a $V_H$ and $V_L$ heterodimer (Fv).

Determination of the three-dimensional structures of antibody fragments by X-ray crystallography has lead to the realization that variable domains are each folded into a characteristic structure composed of nine strands of closely packed β-sheets. The structure is maintained despite sequence variation in the $V_H$ and $V_L$ domains [Depreval, C., et al., *J. Mol. Biol.* 102:657 (1976); Padlan, E. A., *Q. Rev. Biophys.* 10:35 (1977)]. Analysis of antibody primary sequence data has established the existence of two classes of variable region sequences: hypervariable sequences and framework sequences [Kabat, E. A., et al., *Sequences of Protein of Immunological Interests*, 4th ed. U.S. Dept. Health and Human Services (1987)]. The framework sequences are responsible for the correct β-sheet folding of the $V_H$ and $V_L$ domains and for the interchain interactions that bring the domains together. Each variable domain contains three hypervariable sequences which appear as loops. The six hypervariable sequences of the variable region, three from the $V_H$ and three from the $V_L$ form the antigen binding site, and are referred to as a complementarity determining region (CDRs).

By cloning the variable region genes for both the $V_H$ and $V_L$ chains of interest, it is possible to express these proteins in bacteria and rapidly test their function. One method is by using hybridoma mRNA or splenic mRNA as a template for PCR amplification of such genes [Huse, et al., *Science* 246:1276 (1989)]. Thus, one can readily screen an antibody to insure that it has a sufficient binding affinity for the antigen. The binding affinity ($K_d$) should be at least about $10^{-7}$ 1/M, more preferably at least about $10^{-8}$ 1/M.

In one preferred embodiment, the genes encoding the light chain and heavy chain encode a linker to make a single chain antibody (sFv). FIG. 1 shows the construction of the sFv sequences of this invention. The sFv will properly fold even under the reducing conditions sometimes encountered intracellularly. The sFv typically comprises a single peptide with the sequence $V_H$-linker-$V_L$ or $V_L$-linker-$V_H$. The linker is chosen to permit the heavy chain and light chain to bind together in their proper conformational orientation. See for example, Huston, J. S., et al., *Methods in Enzym.* 203:46–121 (1991), which is incorporated herein by reference. Thus, the linker should be able to span the 3.5 nm distance between its points of fusion to the variable domains without distortion of the native Fv conformation. The amino acid residues constituting the linker must be such that it can span this distance and should be 5 amino acids or larger. The amino acids chosen also need to be selected so that the linker is hydrophilic so it does not get buried into the antibody. Preferably, the linker should be at least about 10 residues in length. Still more preferably it should be about 15 residues. While the linker should not be too short, it also should not be too long as that can result in steric interference with the combining site. Thus, it preferably should be 25 residues or less. The linker (Gly-Gly-Gly-Gly-Ser)$_3$ (SEQ ID NO: 1) is a preferred linker that is widely applicable to many antibodies as it provides sufficient flexibility. [Other linkers include Glu Ser Gly Arg Ser Gly Gly Gly Gly Ser Gly Gly Gly Gly Ser (SEQ ID NO:2), Glu Gly Lys Ser Ser Gly Ser Gly Ser Glu Ser Lys Ser Thr (SEQ ID NO:3), Glu Gly Lys Ser Ser Gly Ser Gly Ser Glu Ser Lys Ser Thr Gln (SEQ ID NO:4), Glu Gly Lys Ser Ser Gly Ser Gly Ser Glu Ser Lys Val Asp (SEQ ID NO:5), Gly Ser Thr Ser Gly Ser Gly Lys Ser Ser Glu Gly Lys Gly (SEQ ID NO:6), Lys Glu Ser Gly Ser Val Ser Ser Glu Gln Leu Ala Gln Phe Arg Ser Leu Asp (SEQ ID NO:7), and Glu Ser Gly Ser Val Ser Ser Glu Glu Leu Ala Phe Arg Ser Leu Asp (SEQ ID NO: 8)]. Alternatively, one can take a 15-mer, such as the (Gly-Gly-Gly-Gly-Ser)$_3$ (SEQ ID NO: 1) linker, (although any sequence can be used) and randomize the amino acids in the linker through mutagenesis. Then the antibodies with the different linkers can be pulled out with phage display vectors and screened for the highest affinity single chain antibody generated.

Preferably, the gene does not encode the normal leader sequence for the variable chains, as it is preferable that the antibody does not encode a leader sequence. The nucleotides coding for the binding portion of the antibody preferably do not encode the antibody's secretory sequences (i.e. the sequences that cause the antibody to be secreted from the cell). Such sequences can be contained in the constant region. Preferably, one also does not use nucleotides encoding the entire constant region of the antibodies. More preferably, the gene encodes less than six amino acids of the constant region.

As discussed above, the immune system can be used to produce an antibody which will bind to a specific molecule such as a target protein by standard immunological techniques. For example, using the protein or an immunogenic fragment thereof or a peptide chemically synthesized based upon such protein or fragment. Any of these sequences can be conjugated, if desired, to keyhole limpet hemocyanin (KLH) and used to raise an antibody in animals such as a mice, rabbits, rats, and hamsters. Thereafter, the animals are sacrificed and their spleens are obtained. Monoclonal antibodies are produced by using standard fusion techniques for forming hybridoma cells. See, Kohler, G., et al. *Nature* 256:495 (1975). This typically involves fusing an antibody-producing cell (i.e., spleen) with an immortal cell line such as a myeloma cell to produce the hybrid cell.

Another method for preparing antibodies is by in vitro immunization techniques, such as using spleen cells, e.g., a culture of murine spleen cells, injecting an antigen, and then screening for an antibody produced to said antigen. With this method, as little as 0.1 micrograms of antigen can be used, although about 1 microgram/milliliter is preferred. For in vitro immunization, spleen cells are harvested, for example, mice spleen cells, and incubated at the desired amount, for example, $1\times10^7$ cells/milliliter, in medium plus with the desired antigen at a concentration typically around 1 microgram/milliliter. Thereafter, one of several adjuvants depending upon the results of the filter immunoplaque assay are added to the cell culture. These adjuvants include N-acetylmuramyl-L-alanyl-D-isoglutamine [Boss, *Methods in Enzymology* 121:27–33 (1986)], Salmonella typhimurium mitogen [Technical Bulletin, Ribi ImmunoChem. Res. Inc., Hamilton, Mont.] or T-cell condition which can be produced by conventional techniques [See, Borrebaeck, C. A. K., *Mol. Immunol.* 21:841–845 (1984); Borrebaeck, C. A. K., *J. Immunol.* 136:3710–3715 (1986)] or obtained commercially, for example, from Hannah Biologics, Inc. or Ribi ImmunoChem. Research Inc. The spleen cells are incubated with the antigen for four days and then harvested.

Single cell suspensions of the in vitro immunized mouse spleen cells are then incubated, for example on antigen-nitrocellulose membranes in microfilter plates, such as those available from Millipore Corp. The antibodies produced are detected by using a label for the antibodies such as horseradish peroxidase-labeled second antibody, such as rabbit anti-mouse IgA, IgG, and IgM. In determining the isotype of the secreted antibodies, biotinylated rabbit anti-mouse heavy chain specific antibodies, such as from Zymed Lab., Inc. can be used followed by a horseradish peroxidase-avidin reagent, such as that available from Vector Lab.

The insoluble products of the enzymatic reaction are visualized as blue plaques on the membrane. These plaques are counted, for example, by using 25 times magnification. Nitrocellulose membrane of the microfilter plaques readily absorb a variety of antigens and the filtration unit used for the washing step is preferred because it facilitates the plaque assay.

One then screens the antibodies by standard techniques to find antibodies of interest. Cultures containing the antibodies of interest are grown and induced and the supernatants passed through a filter, for example, a 0.45 micromiter filter and then through a column, for example, an antigen affinity column or an anti-tag peptide column. The binding affinity is tested using a mini gel filtration technique. See, for example, Niedel, J., *Biol. Chem.* 256:9295 (1981). One can also use a second assay such as a radioimmunoassay using magnetic beads coupled with, for example, anti-rabbit IgG to separate free $^{125}$I-labeled antigen from $^{125}$I-labeled antigen bound by rabbit anti-tag peptide antibody. In a preferred alternative one can measure "on" rates and "off" rates using, for example, a biosensor-based analytical system such as "BIAcore" from Pharmacia Biosensor AB [See, *Nature* 361:186–187 (1993)].

This latter technique is preferred over in vivo immunization because the in vivo method typically requires about 50 micrograms of antigen per mouse per injection and there are usually two boosts following primary immunization for the in vivo method.

Alternatively, one can use a known antibody to the target protein. Thus, one can obtain antibodies to the desired target protein. Thereafter, a gene to at least the antigen binding portion of the antibody is synthesized as described below. The gene preferably will not contain the normal signal peptide sequences. In some preferred embodiments it will also encode an intracellular localization sequence such as one for the endoplasmic reticulum, nucleus, nucleolar, etc. When you want expression in the ER normal antibody secretory system such as the endoplasmic reticulum-golgi apparatus a leader sequence should be used. To retain such antibodies at a specific place, a localization sequence such as the KDEL sequence (ER retention signal) may be used. In some embodiments the antibody gene preferably also does not encode functional secretory sequences.

Antibody genes can be prepared based upon the present disclosure by using known techniques.

Using any of these antibodies, one can construct $V_H$ and $V_L$ genes. For instance, one can create $V_H$ and $V_L$ libraries from murine spleen cells that have been immunized either by the above-described in vitro immunization technique or by conventional in vivo immunization and from hybridoma cell lines that have already been produced or are commercially available. One can also use commercially available $V_H$ and $V_L$ libraries. One method involves using the spleen cells to obtain mRNA which is used to synthesize cDNA. Double stranded cDNA can be made by using PCR to amplify the variable region with a degenative N terminal V region primer and a J region primer or with $V_H$ family specific primers, e.g., mouse-12, human-7.

For example, the genes of the $V_H$ and $V_L$ domains of the desired antibody such as one to IL-2Rα can be clone and sequenced. The first strand cDNA can be synthesized from, for example, total RNA by using oligo dT priming and the Moloney murine leukemia virus reverse transcriptase according to known procedures. This first strand cDNA is then used to perform PCR reactions. One would use typical PCR conditions, for example, 25 to 30 cycles using e.g. Vent polymerase to amplify the cDNA of the immunoglobulin genes. DNA sequence analysis is then performed. [Sanger, et al., *Proc. Natl. Acad. Sci. USA* 79:5463–5467 (1977)].

Both heavy chain primer pairs and light chain primer pairs can be produced by this methodology. One preferably inserts convenient restriction sites into the primers to make cloning easier.

As an example of the strategy that is used, heavy chain primer pairs consist of a forward $V_H$ primer and a reverse $J_H$ primer, each containing convenient restriction sites for cloning can be prepared. One could use, for example, the Kabat data base on immunoglobulins [Kabat, et al., supra] to analyze the amino acid and codon distribution found in the seven distinct human $V_H$ families. From this, a 35 base pair universal 5' $V_H$ primer is designed. One could use a primer such as TTTGCGGCCGCTCAGGTGCA(G/A)CTG CTCGAGTC(T/C)GG (SEQ ID NO:9), which is degenerate for two different nucleotides at two positions and will anneal to the 5' end of FR1 sequences. A restriction site such as the 5' Not I site (left-underlined) can be introduced for cloning the amplified DNA and is located 5' to the first codon to the $V_H$ gene. Similarly, a second restriction site such as an internal XhoI site can be introduced as well (right-underlined).

Similarly, a 66-base pair $J_H$ region oligonucleotide can be designed for reverse priming at the 3' end of the heavy chain variable gene, e.g., AGATCCGCCGCCACCGCTCCCAC-CACCTCCGGAGCCACCGCCACCTGAGGTGACC GTGACC (A/G) (G/T) GGT (SEQ ID NO: 10). This primer additionally contains a 45 nucleotide sequence that encodes a linker, such as the (Gly-Gly-Gly-Gly-Ser)$_3$ (SEQ ID NO: 1) interchange linker. This primer contains two degenerate positions with two nucleotides at each position based on the nucleotide sequence of the six human $J_H$ region minigenes. Restriction sites can be used, for example, a BspEI site (left-underlined) is introduced into the interchange linker for cohesive end ligation with the overlapping forward $V_{kappa}$ primer. An internal BsTEII site (right-underlined) is introduced as well for further linker exchange procedures.

A similar strategy using the 45 nucleotide interchange linker is incorporated into the design of the 69 nucleotide human $V_{kappa}$ primer. There are four families of human $V_{kappa}$ genes. The 5' $V_{kappa}$ primer GGTGGCGGTGGC TCCGGAGGTGGTGGGAGCGGTGGCGGCGGATCT GAGCTC (G/C)(T/A)G(A/C)TGACCCAGTCTCCA (SEQ ID NO: 11), which will anneal to the 5' end of the FR1 sequence is degenerate at 3 positions (2 nucleotides each). The interchange linker portion can contain a BspEI site for cohesive end cloning with the reverse $J_H$ primer, other restriction sites can also be used. An internal SacI site (right-underlined) can be introduced as well to permit further linker exchange procedures.

The reverse 47 nucleotide $C_{kappa}$ primer (Kabat positions 109–113) GGG TCTAGACTCGAGGATCCTTATTA ACGCGTTGGTGCAGCCACAGT (SEQ ID NO: 12) is designed to be complementary to the constant regions of kappa chains (Kabat positions 109–113). This primer will anneal to the 5' most end of the kappa constant region. The primer contains an internal MluI site (right-underlined) proceeding two stop codons. In addition, multiple restriction sites such as Bam HI XhoI/XbaI (left-underlined) can be introduced after the tandem stop codons. A similar reverse nucleotide C-kappa primer such as a 59 nucleotide primer can also be designed that will contain a signal for a particular intracellular site, such as a carboxy terminal endoplasmic reticulum retention signal, Ser-Glu-Lys-Asp-Glu-Leu (SEQ ID NO: 13) (SEKDEL), GGG TCTAGACTCGAGGATCCTTATTACAGCT CGTC-CTTTTCGCTTGGTGCAGCCACAGT (SEQ ID NO: 14). Similar multiple restriction sites (Bam HI XhoI/XbaI) can be introduced after the tandem stop codons.

After the primary nucleotide sequence is determined for both the heavy and kappa chain genes and the germ line genes are determined, a PCR primer can then be designed, based on the leader sequence of the $V_H$ 71-4 germ line gene. For example, the $V_H$ 71-4 leader primer TTTA CCATGGAACATCTGTGGTTC (SEQ ID NO: 15) contains a 5' NcoI site (underlined). This leader primer (P-L) is used in conjunction with a second $J_H$ primer for PCR amplification experiments. The 35 base pair $J_H$ region oligonucleotide is designed to contain the same sequence for reverse priming at the 3' end of the heavy chain variable gene, TTA GCGCGCTGAGGTGACCGTGACC(A/G)(G/T)GGT (SEQ ID NO: 16). This primer contains two degenerate positions with two nucleotides at each position. A BssH II site (left-underlined) 3' to and immediately adjacent to the codon determining the last amino acid of the J region, allows convenient cloning at the 3' end of the $V_H$ gene. An internal BstE II site (right-underlined) is introduced as well. This sequence is used to amplify the $V_L$ sequence. The fragments amplified by the P-L (leader primer) and P linker (reverse primer) and P-K ($V_2$ primer) and P-CK primers (reverse CK primer) are then cloned into an expression vector, such as the pRc/CMV (Invitrogen) and the resultant recombinant contains a signal peptide, $V_H$ interchain linker and $V_L$ sequences under the control of a promoter, such as the CMV promoter. The skilled artisan can readily choose other promoters that will express the gene in the cell system of choice, for example, a mammalian cell, preferably human cells.

To prepare anti-Tac sFv's one could use the primer sequences A(SEQ ID NO:49) and B(SEQ ID NO:50) for $V_H$, C(SEQ ID NO:51) and D(SEQ ID NO:52) for $V_L$, which are set forth in Table 3. A preferred interchain linker for this antibody would be (gly-gly-gly-gly-ser)$_3$ and can readily be prepared by peptide synthesizers or excised and amplified by PCR from a plasmic containing this sequence. The sFv can be assembled from the various fragment ($V_H$, $V_L$, and interchain linker) by overlap extension [Horton, R. M., et al. Gene 77:61–68 (1989)] followed by amplification with primers SEQ ID NO:49 and SEQ ID NO:52. The complete sequence can be confirmed by the dideoxy chain termination method of Sanger [Proc. Natl. Acad. Sci. USA 74:5463–5467 (1977)].

Accordingly, as used herein the gene for the antibody can encompass genes for the heavy chain and light chain regions. In addition, the gene is operably linked to a promoter or promoters which results in its expression. Promoters that will permit expression in mammalian cells are well known and include cytomegalovirus (CMV) intermediate early promoter, a viral LTR such as the rous sarcoma virus LTR, HIV-LTR, HTLV-1 LTR, the simian virus 40 (SV40) early promoter, E. coli lac UV5 promoter and the herpes simplex tk virus promoter. This DNA sequence is described as the "antibody cassette".

However, there are instances where a greater degree of intracellular specificity is desired. For example with IL-2Rα, there can be competition from a 40 kD protein, but which does interfere with the antibody that does not contain the KDEL sequence. Thus, one preferably uses localization sequences in such instances. Our antibodies can be delivered intracellularly and can be expressed there and bind to a target protein.

Localization sequences have been divided into routing signals, sorting signals, retention or salvage signals and membrane topology-stop transfer signals. [Pugsley, A. P., Protein Targeting, Academic Press, Inc. (1989)]. For example, in order to direct the antibody to a specific location, one can use specific localization sequences. For example, signals such as Lys Asp Glu Leu (SEQ ID NO: 17) [Munro, et al., Cell 48:899–907 (1987)] Asp Asp Glu Leu (SEQ ID NO:18), Asp Glu Glu Leu (SEQ ID NO: 19), Gln Glu Asp Leu (SEQ ID NO:20) and Arg Asp Glu Leu (SEQ ID NO:21) [Hangejorden, et al., J. Biol. Chem. 266:6015 (1991), for the endoplasmic reticulum; Pro Lys Lys Lys Arg Lys Val (SEQ ID NO:22) [Lanford, et al. Cell 46:575 (1986)] Pro Gln Lys Lys Ile Lys Ser (SEQ ID NO:23) [Stanton, L. W., et al., Proc. Natl. Acad. Sci USA 83:1772 (1986); Gln Pro Lys Lys Pro (SEQ ID NO:24) [Harlow, et al., Mol. Cell Biol. 5:1605 1985], Arg Lys Lys Arg (SEQ ID NO:58), for the nucleus; and Arg Lys Lys Arg Arg Gln Arg Arg Arg Ala His Gln (SEQ ID NO:25), [Seomi, et al., J. Virology 64:1803 (1990)], Arg Gln Ala Arg Arg Asn Arg Arg Arg Arg Trp Arg Glu Arg Gln Arg (SEQ ID NO:26) [Kubota, et al., Biochem. and Biophy, Res. Comm. 162:963 (1989)], Met Pro Leu Thr Arg Arg Arg Pro Ala Ala Ser Gln Ala Leu Ala Pro Pro Thr Pro (SEQ ID NO:27) [Siomi, et al., Cell 55:197 (1988)] for the nucleolar region; Met Asp Asp Gln Arg Asp Leu Ile Ser Asn Asn Glu Gln Leu Pro (SEQ ID NO:28), [Bakke, et al., Cell 63:707–716 (1990)] for the endosomal compartment. See, Letourneur, et al., Cell 69:1183 (1992) for targeting liposomes. Myristolation sequences, can be used to direct the antibody to the plasma membrane. Table I, sets forth the amino-terminal sequences for known N-myristoylproteins and their subcellular location. In addition, as shown in Table 2 below, myristoylation sequences can be used to direct the antibodies to different subcellular locations such as the nuclear region. Localization sequences may also be used to direct antibodies to organelles, such as the mitochondria and the Golgi apparatus. The sequence Met Leu Phe Asn Leu Arg Xaa Xaa Leu Asn Asn Ala Ala Phe Arg His Gly His Asn Phe Met Val Arg Asn Phe Arg Cys Gly Gln Pro Leu Xaa (ID NO:29) can be used to direct the antibody to the mitochondrial matrix. (Pugsley, supra). See, Tang, et al., J. Bio. Chem. 207:10122, for localization of proteins to the Golgi apparatus.

TABLE 2

| AMINO-TERMINAL SEQUENCE[4] | SUBCELLULAR LOCATION[5] | PROTEIN | REFERENCE |
|---|---|---|---|
| GCVCSSNP (SEQ ID NO: 30) | PM | p56$^{USTRATCK}$ | Marchildon, et al. Proc. Natl. Acad. Sci. USA 81:7679–7682 (1984) Voronova, et al. Mol. Cell. Biol. 4:2705–2713 (1984) |
| GQTVTTPL (SEQ ID NO: 31) | PM | Mul. V gag | Henderson, et al., Proc. Natl. Acad. Sci. USA 89:339–343 (1987) |
| GQELSQHE (SEQ ID NO: 32) | PM | M-PMV gag | Rhee, et al, J. Virol 61:1045–1053 (1987) Schultz, et al. J. virol. 46:355–361 (1983) |
| GNSPSYNP (SEQ ID NO: 33) | PM | BLV gag | Schultz, et al., J. virol 133:431–437 (1984) |
| GVSGSKGQ (SEQ ID NO: 34) | PM | MMTV gag | Schutz, et al. supra |
| GQTITTPL (SEQ ID NO: 35) | PM | FCL. V gag | Schutz, et al., supra |
| GQTLTTPL (SEQ ID NO: 36) | PM | BaEV gag | Schultz, et al. supra |
| GQIFSRSA (SEQ ID NO: 37) | PM | HTLV-I gag | Ootsuyama, et al., Jpn J. Cancer Res. 76:1132–1135 (1985) |
| GQIHGLSP (SEQ ID NO: 38) | PM | HTLV-II gag | Ootsuyama, et al., supra |
| GARASVLS (SEQ ID NO: 39) | PM | HIV (HTLV-III) gag | Ratner, et al. Nature 313:277–284 (1985) |
| GCTLSAEE (SEQ ID NO: 40) | PM | bovine brain G$_o$ α-subunit | Schutz, et al., Biochem. Biophys. Res. Commun. 146:1234–1239 (1987) |
| GQNLSTSN (SEQ ID NO: 41) | ER | Hepatitis B Virus pre-Sl | Persing, et al., J. Virol. 61:1672–1677 (1987) |
| GAALTILV (SEQ ID NO: 42) | N | Polyoma Virus VP2 | Streuli, et al., Nature 326:619–622 (1987) |
| GAALTLLG (SEQ ID NO: 43) | N | SV40 Virus VP2 | Streuli, et al., supra |

TABLE 2-continued

| AMINO-TERMINAL SEQUENCE[4] | SUBCELLULAR LOCATION[5] | PROTEIN | REFERENCE |
|---|---|---|---|
| GAQVSSQK (SEQ ID NO: 44) | S, ER | Poliovinis VP4 | Chow, et al., Nature 327:482–486 (1987) Paul, et al., Proc. Natl. Acad. Sci. USA 84:7827–7831 (1987) |
| GAQLSRNT (SEQ ID NO: 45) | S, ER | Bovine Enterovirus VP4 | Paul, et al., supra |
| GNAAAAKK (SEQ ID NO: 46) | G, S, N, C | cAMP-dependent kinuse | Carr, et al., Proc. Natl. Acad. Sci. USA 79:6128–6131 (1982) |
| GNEASYPL (SEQ ID NO: 47) | S, C | calcincurin B | Aitken, et al. FEBS Leu. 150:314–318 (1982) |
| GSSKSKPK (SEQ ID NO: 48) | PM, C | p60$^{SFC}$ | Schultz, et al., Science 227:427–429 |

[4]To assist the reader, the standard single letter amino acid code is used in the Table, the amino acid sequences using the three letter code are set out in the Sequence Listing.
[5]Abbreviations are PM, plasma membranes, G. Golgi; N, Nuclear; C, Cytoskeleton; s, cytoplasm (soluble); M, membrane.

The antibody cassette is delivered to the cell by any of the known means. One preferred delivery system is described in U.S. patent application Ser. No. 08/199,070 by Marasco filed Feb. 22, 1994, which is incorporated herein by reference. This discloses the use of a fusion protein comprising a target moiety and a binding moiety. The target moiety brings the vector to the cell, while the binding moiety carries the antibody cassette. Other methods include, for example, Miller, A. D., Nature 357:455–460 (1992); Anderson, W. F., Science 256:808–813 (1992); Wu, et al, J. of Biol. Chem. 263:14621–14624 (1988). For example, a cassette containing these antibody genes, such as the sFv gene, can be targeted to a particular cell by a number of techniques. In the discussion below we will discuss the sFv genes coding for IL-2Rα antibodies, which would be preferably introduced into human T-cells. Other delivery methods include the use of microcatheters, for example, delivering the vector in a solution which facilitates transfection.

The intracellular expression of the antibody permits it to bind the target. This disrupts the functioning of the target, e.g., a protein, including its undesired function. For instance, expressing the sFv of an antibody to IL-2Rα can intracellularly block the transport of the IL-2Rα chain and therefore, the formation of the IL-2 high affinity receptor. In so doing one may be able to inhibit the IL-2-dependent expansion of malignant, autoreactive or allograft-specific T cells.

In theory, there are multiple points within the secretory pathway at which an intrabody can be placed to bind and divert a trafficking protein from its ultimate destination. The ER is a preferred location because it permits trapping proteins early in their biosynthesis and creates potential for the rapid disposal of immune complexes by degradative systems within the ER [Klausner, R. D. & Sitia, R., Cell 62:611–614 (1990)]. Peptide signals required for the ER-retention of soluble proteins are well characterized and the carboxy terminal tetrapeptide Lys-Asp-Glu-Leu (KDEL) [Munroe, S. & Pehham, H. B., Cell 48:899–907 (1987)] is a preferred sequence. The efficiency of the ER retention system is in part due to the existence of a retrieval mechanism which returns KDEL-tagged proteins to the ER if and when they escape into the cis golgi network [Rothman, J. E. & Orci, L., Nature 355:409–415 (1992)]. The ER is also the natural site of antibody assembly as it is the residence to molecular chaperones such as BiP and GRP94, which assist in the correct folding of immunoglobulin molecules [Melnick, J., et al., Nature 370:373–375 (1994)]. The ER also offers the advantage that ER-resident proteins often show extended half-lives.

Whereas, the β and γ chains (IL-2Rβ and IL-2Rγ) are constitutively expressed on resting T-cells where they form a receptor of intermediate affinity, the 55kD α chain (IL-2Rα) is typically only transiently expressed following engagement of the T-cell receptor. Moreover, it is upregulated in certain T and B cell leukemias. Thus, the α chain is a preferred target when specificity for an IL-2Rα associated cell is the target over the β or γ chains because blocking the β and γ chains can kill other resting T-cells which are dependent on them. In addition, even with targeting the a chain there are certain cells that require IL-2 or IL-2Rα, for example, Kit225 cells, C8166 cells, MT-2 cells, HUT-102 cells, etc. as opposed to Jurkat cells, which does not normally express IL-2Rα, but will do so when treated with phorbol diester. While the upregulation of these chains, particularly, the IL-2Rα chain, is undesired. It will not in all instances be desired to knock out the receptor in all cells expressing it. Accordingly, one preferably uses an inducible promoter, which is turned on predominantly in the cells you want to kill, for example, leukemic cells. For example, one can use a promoter that is induced by radiation to selectively turn on the desired cells. Another strategy to maximize the targeting of the specific cells is to use a delivery system, wherein the targeting moiety targets, for example, a second protein associated with the target cell.

The IL-2R intrabodies, for example, the IL-2Rα intrabodies bind to and form a complex with the receptor chains intracellularly. By use of appropriate targeting signals, for example, the endoplasmic reticulum retention signal, such as KDEL, one can further tailor the intrabodies. For example, one can prepare antibodies for IL-2Rα (Tac)(1) without any targeting signal (sFvTac) and (2) with an endoplasmic reticulum retention signal (KDEL) (sFvTacKDEL). Genes encoding these sFvs can then intracellularly inserted into mammalian cells.

Figure 6:
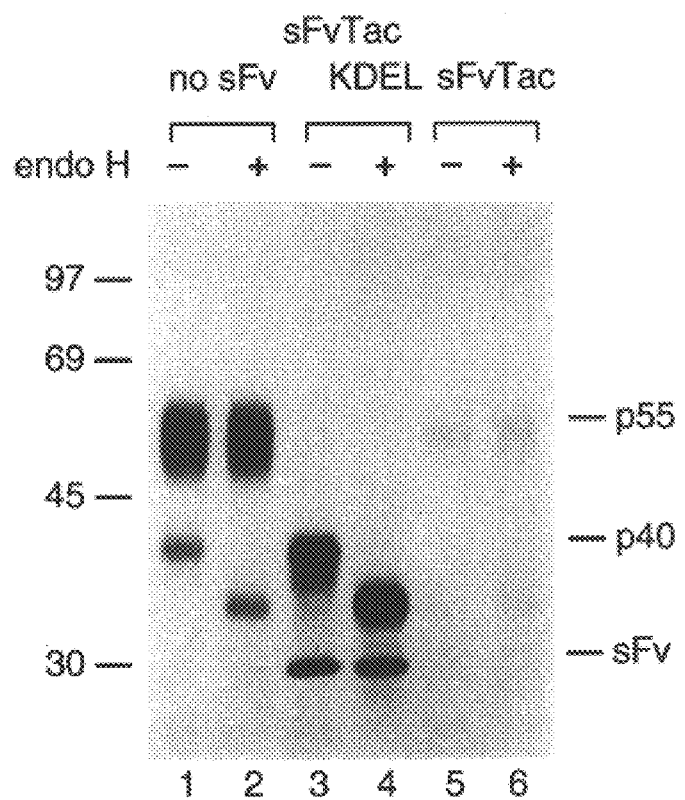
FIG. 6 is an autoradiogram showing endoglycosidase H sensitivity of IL-2Rα immunoprecipitated with mAb 7G7/B6 from Jurkat cells expressing no sFv (lanes 1 and 2), sFvTacKDEL lanes 3 and 4) and sFvTac (lanes 5 and 6). The p55 and p40 forms of IL-2Rα are indicated, as is the 30 kD sFvTacKDEL.
Figures 5A, 5B, 5C:
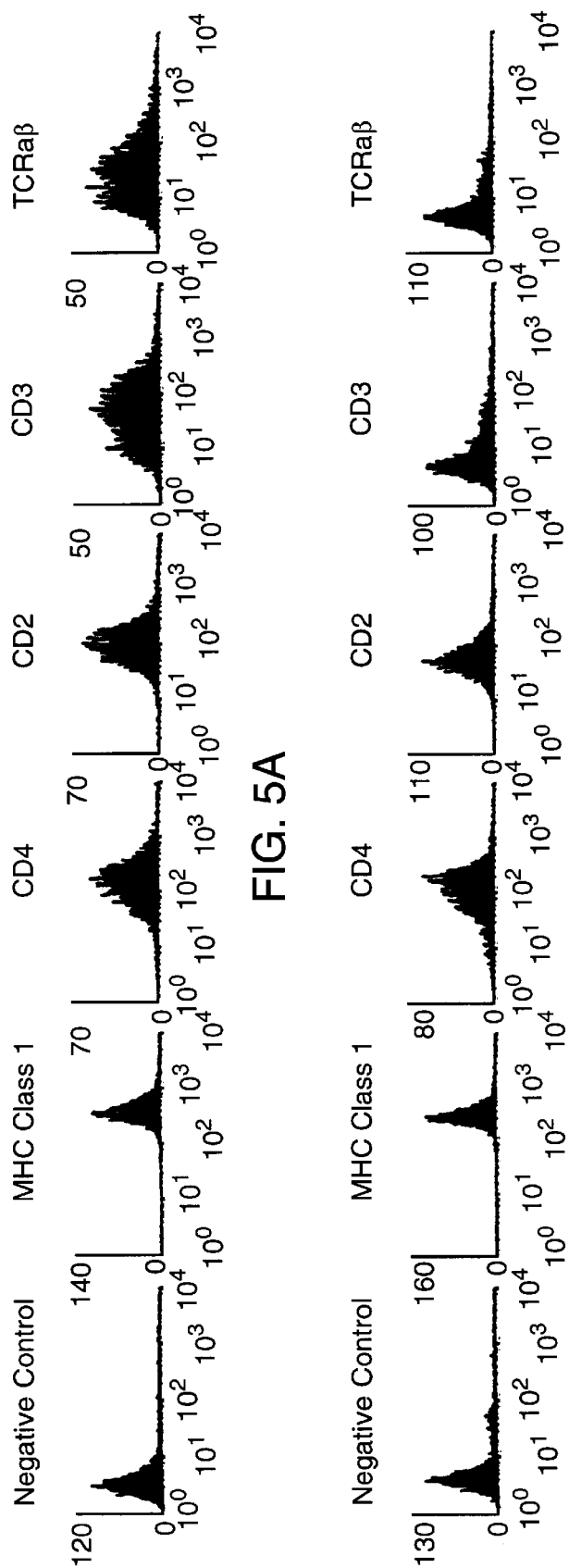
FIGS. 5A–5F show FACS analysis of MHC class 1, the T cell antigen receptor, CD2, CD3 and CD4 in the parental Jurkat cell line (row a) and a selection of transfectant clones expressing sFvTac (rows b, c) or sFvTacKDEL (rows d–f).
Figure 5D:
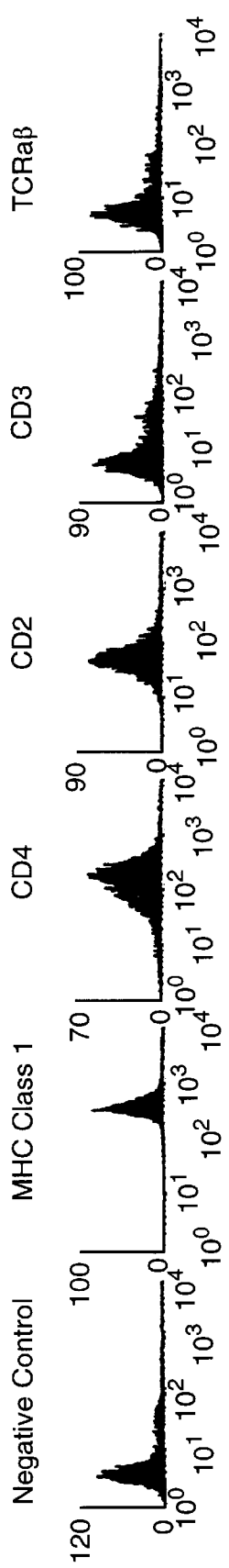
Figure 5E:
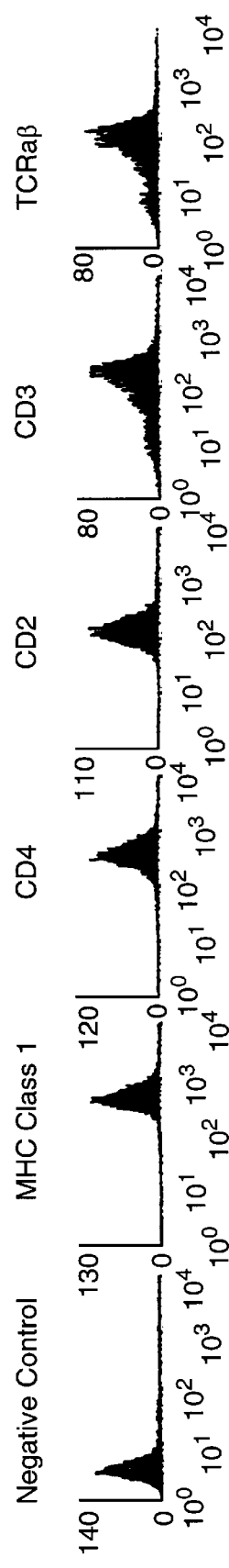
Figure 5F:
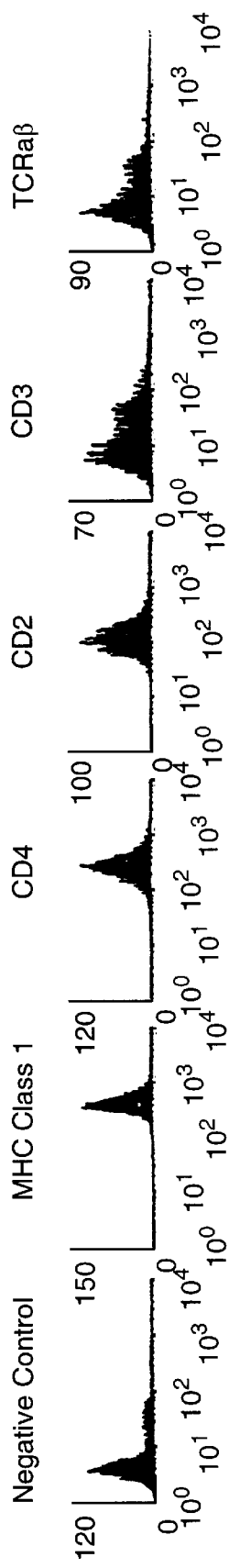

Both intrabodies are expressed inside cells. However, the sFv Tac KDEL intrabody is retained in the ER, whereas, the sFv Tac intrabody continues to move through the cell. As a consequence, the two intrabodies bind to and form complexes at different intracellular sites. For example, the ER intrabody (sFvTacKDEL) binds and holds the receptor chain in the ER. For example, the sFvTacKDEL intrabody coprecipitates with IL-2Rα, suggesting a physical interaction between the two proteins inside the cell. Furthermore, IL-2Rα is detectable within these cells as an immature 40 kD form that is sensitive to endoglycosidase-H. See FIG. 6, lanes 4 and 4. The absence of complex carbohydrates, which are added in the golgi and would render the protein resistant to endo H, thereby show that the 40 kD precursor is held in an early golgi or pre-golgi compartment. FIG. 6.

Figure 4:
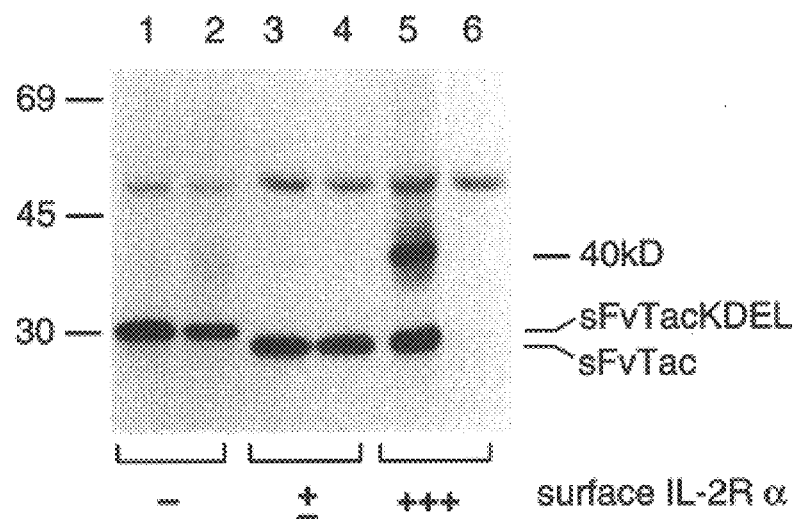
FIG. 4 is an autoradiogram showing SDS-PAGE analysis of sFvTacKDEL (lanes 1 and 2) and sFvTac (lanes 3–5) immunoprecipitated from PHA/PMA stimulated Jurkat cells. Non-transfected Jurkat cells are analyzed in lane 6. The cell surface expression of IL-2Rα as determined by FACS analysis is summarized below each lane. Normal expression of IL-2Rα by the sFvTac clone is shown in lane 5. The upper band present in all lanes is non-specific and not p55 IL-2Rα.

The sFvTac intrabody, which lacks an ER retention signal, is also not efficiently secreted. See also Marasco, W. A., et al., Proc. Natl. Acad. Sci. USA 90:7889–7893 (1993), which shows similar results with other single chain antibodies. And like sFvTacKDEL, this intrabody downregulates IL-2Rα. However, it gave a "leaky" phenotype, i.e., low level expression of IL-2Rα at the cell surface. See FIG. 3, panel D. We believe this is because of competition that arises in the cellular compartment where binding occurs. Thus, in a proportion of Jurkat clones expressing sFvTac, the activity of the intrabody in binding IL-2rα can be confounded by the formation of competing complexes between sFvTac and an unidentified 40 kD protein. FIG. 4, lane 5. The interfering protein, which binds to sFvTac, apparently decreasing its interaction with IL-2Rα, is never associated with sFvTacK-DEL and likely resides in a post ER compartment. Thus, the use of the KDEL sequence increases the desired binding of the sFvTac by maintaining it within the ER.

In addition, the resultant antibody-antigen complexes formed such as the IL-2Rα complexes formed with the two intrabodies, sFvTac and sFvTacKDEL, may have different fates. Complexes formed with sFvTacKDEL are more stably retained in the ER, whereas the IL-2Rα complexed to sFvTac appear in comparison to be rapidly degraded. The rapid clearance of intracellular immune complexes can in certain instances benefit the cell, avoiding the build up of unwanted protein within the secretory system.

Thus, multiple aspects of intrabody behavior, including stability, efficacy, binding specificity and intracellular fate of the two proteins can be affected by the presence or absence of a localization sequence. With IL-2Rα the ER-resident intrabody (sFvTacKDEL) is more effective at blocking the cell surface transport of IL-2Rα than sFvTac. The presence of the sFvTacKDEL intrabody completely abrogates the cell surface expression of IL-2Rα in PMA stimulated Jurkat cells. See FIG. 4. As the regulation of IL-2Rα in Jurkat cells mimics that seen in peripheral blood T cells, similar results are achievable in primary T cells from normal or leukaemic subjects. As described further below, inducible expression of the intrabody is preferable in such cells which, unlike Jurkat cells, are dependent on IL-2 for long term survival. The decision on an appropriate intracellular localization sequence can readily be determined by the skilled artisan based on the target and the cell based upon the present disclosure.

For example, using the above-described methodology, one can treat mammals, preferably humans, suffering from ailments caused by the expression or overexpression of specific proteins, such as T and B cell leukaemias, most notably HTLV-1 associated adult T cell leukemia. For example, one can target the antigens with an antibody that will specifically bind to such antigen. One delivers an effective amount of a gene capable of expressing the antibody, under conditions which will permit its intracellular expression, to cells susceptible to expression of the undesired target antigen. In certain instances this method can be used as a prophylactic treatment to prevent or make it more difficult for such cells to be adversely affected by the undesired antigen, for example, by preventing processing of the protein and expression of the receptor. Where a number of targets exist, one preferred target is proteins that are processed by the endoplasmic reticulum. Intracellular delivery of any of the antibody genes can be accomplished by using procedures such as gene therapy techniques such as described above. The antibody can be any of the antibodies as discussed above. We discuss herein the use of this system to deliver antibody genes to T or B cells, for example, the T cells of a leukaemic mammal, for example, a human with T cell leukaemia, but it should be understood that based upon the present disclosure, one can readily adapt such an approach to other systems, for example, an individual with other receptor abnormalities. In addition, this system can be used to transiently prevent receptor expression and thereby block undesired T-cell mediated reactions such as allograft rejections.

For certain cells, such as where, the protein, for example, Interleukin-2 and hence the IL-2 receptor, are vital for long-term survival means are necessary to selectively administer the intrabody solely to aberrant cells. Numerous means exist as discussed above, including microcatheters, inducible promoters, and conjugates. For example, microcatheters can be used to deliver a solution containing the antibody cassette to the cells. Alternatively, the expression of the antibody can be controlled by an inducible promoter. Such a promoter could be activated by an effect of the target, or an outside source such as radiation. In cells such as malignant "cocktails" containing a mixture of antibodies can be used to target a number selection can lead to establishment of the cells that "turn-off" an intrabody, or no longer need the receptor for survival. With those cells the use of proteins at one time is desired because it makes it more difficult for mutants to evolve which will produce proteins capable of avoiding the antibody. For example, also targeting the β chain, or a different cellular function. Mik $\beta_1$ is a Mab against IL-2R β chain. [Kreitman, R. J., et al., *J. of Immun.* 149:2810–2815 (1992); Hakimi, J., et al., *J. of Immun.* 147:1352–1359 (1991)]. Such "cocktails" can be administered together or by co-transfections. It is preferred that no more than about three proteins in the same intracellular region are targeted, preferably no more than about two. As long as another intracellular target is in a different cellular region, i.e., nucleus vs endoplasmic reticulum, it can also be targeted without having a detrimental effect on antibody production. This could be done using different localization sequences. If some target is not bound to the antibody at one location and, for instance, is further processed, it can be targeted at a subsequent location. Alternatively one could use multiple antibodies to target different epitopes of molecules.

Finally, antibody conjugates can be used to target aberrant cells. For example, genes can be delivered using a cell-specific gene transfer mechanism, which uses receptor-mediated endocytosis to carry RNA or DNA molecules into cells. For example, using an antibody against a receptor on the aberrant cell.

The antibodies that are used to target the cells can be coupled to a binding moiety to form an antibody-binding moiety by ligation through disulfide bonds after modification with a reagent such as succinimidyl-3-(2-pyridyldithio) proprionate (SPDP). The antibody-binding moiety complexes are produced by mixing the fusion protein with a moiety carrying the antibody cassette i.e. the DNA sequence containing the antibody operably coupled to a promoter such as a plasmid or vector. An alternative vector uses polyysine as a binding moiety.

As aforesaid, ligation with the antibodies can be accomplished using SPDP. First dithiopyridine groups will be introduced into both antibody or, for example, polylysine by means of SPDP and then the groups, e.g., in the polylysine can be reduced to give free sulfhydryl compounds, which upon mixing with the antibodies modified as described above, react to give the desired disulfide bond conjugates. These conjugates can be purified by conventional techniques such as using cation exchange chromatography. For example, a Pharmacia Mono S column, HR 10/10. These conjugates are then mixed with the antibody cassette under conditions that will permit binding. For example, incubating for one hour at 25° C. and then dialyzation for 24 hours against 0.15 M saline through a membrane with a molecular weight limit as desired. Such membranes can be obtained, for example, from Spectrum Medical Industries, Los Angeles, Calif.

To treat the targeted cells, these vectors can be introduced to the cells in vitro with the transduced cells injected into the mammalian host or the vector can be injected into a mammalian host such as a human where it will bind to with e.g., the T or B cell and then be taken up. To increase the efficiency of the gene expression in vivo, the antibody cassette can be part of an episomal mammalian expression vector. For example, a vector which contains the human Pappova virus (BK) origin of replication and the BK large T antigen for extra-chromosomal replication in mammalian cells, a vector which contains an Epstein-Barr (EB) virus origin of replication and nuclear antigen (EBNA-1) to allow high copy episomal replication. Other mammalian expression vectors such as herpes virus expression vectors, or pox virus expression vectors can also be used. Such vectors are available from a wide number of sources, including Invitrogen Corp. The antibody cassette is inserted into the expression vectors by standard techniques, for example, using a restriction endonuclease and inserting it into a specific site in such mammalian expression vector. These expression vectors can be mixed with the antibody-polylysine conjugates and the resulting antibody-polylysine-expression vector containing antibody cassette complexes can readily be made based upon the disclosure contained herein. One would inject a sufficient amount of these vectors to obtain a serum concentration ranging between about 0.05 µg/ml to 20 µg/ml of antibody conjugate. More preferably between about 0.1 µg/ml to 10 µg/ ml. Still more preferably, between about 0.5 µg/ml to 10 µg/ml.

These vectors can be administered by any of a variety of means, for example, parenteral injection (intramuscular (I.M.), intraperitoneal (I.P.), intravenous (I.V.), intracranial (I.C.) or subcutaneous (S.C.)), oral or other known routes of administration. Parenteral injection is typically preferred.

The materials can be administered in any convenient means, for example, it can be mixed with an inert carrier such as sucrose, lactose or starch. It can be in the form of tablets, capsules and pills. For parenteral administration, it will typically be injected in a sterile aqueous or non-aqueous solution, suspension or emulsion in association with a pharmaceutically-acceptable parenteral carrier such as physiological saline.

The present invention is further illustrated by the following example which is provided to aid in the understanding of the invention and is not construed as a limitation thereof.

EXAMPLE OF THE INVENTION
1. Cells Used

C8166 is an HTLV-1 immortalized T cell line derived by in vitro infection of human cord blood [Salahuddin, S. Z., et al., *Virology* 129:51–64 (1983)] which expresses high levels of IL-2Rα. Jurkat is a human T cell line which does not express IL-2Rα under normal circumstances but can be induced to do so by treatment with phorbol diester [Greene, W. C., et al., *J. Immunol.* 133:1042–1047 (1984)]. C8166 and Jurkat cells were grown in RPMI-1640 supplemented with 10% fetal calf serum and antibiotics. The HD245-332 hybridoma producing the monoclonal antibody (mAb) anti-Tac and was grown in RPMI-1640 supplemented with 20% fetal calf serum and antibiotics. Hybridoma 7G7B6 (ATCC HB8784), producing the mAb 7G7/B6, was grown in Dulbecco's modified Eagle medium supplemented with 10% fetal calf serum and antibiotics. Anti-Tac and 7G7/B6 recognize different epitopes of human IL-2Rα and do not compete for binding [Uchiyama, T., et al., *J. Immunol.* 126:1393–1397 (1981); Rubin, L. A., et al., *Hybridoma* 4:91–102 (1986)].

2. Construction Of The sFvTac Gene

Total cellular RNA and cDNA were prepared from the HD245-332 hybridoma cells as described elsewhere [Marasco, W. A., et al., *J. Clin. Invest.* 90:1467–1478 (1992)]. Heavy and light chain variable regions ($V_H$ and $V_L$) were PCR amplified from the cDNA using Vent polymerase in a 100 µl reaction containing 1.5 µl of $cDNA_2$, 1× Vent reaction buffer (Promega) 0.5 µM each primer, 0.2 mM dNTPs and 2 units Vent polymerase. The primer sequences (A and B for $V_H$ C and D for $V_L$) are listed in Table 3. After an initial 5 minute denaturation at 94° C., the following cycle was repeated 30 times using a thermal cycler (Cetus): 1 minute ramp to 94° C. then 1 minute at 94° C., 1 minute ramp to 52° C. then 2 minutes at 52° C., 2 minute ramp to 72° C. then 2 minutes at 72° C. A final 10 minute incubation at 72° C. was preformed and the samples then stored at 4° C. or −20° C.

The interchain linker (ICL) was prepared by PCR amplification from a plasmid template using the primers E and F (Table 3). The reaction conditions were as above except that Taq polymerase (2 units) and Taq reaction buffer were used, the template was 30 ng of plasmid psFvTat1, the annealing temperature was raised to 56° C. and all ramping and incubation steps were 1 minute in length.

The $V_H$, $V_L$ and ICL fragments were gel purified, ethanol precipitated and resuspended in TE buffer. The single chain antibody gene, called sFvTac, was assembled from the $V_H$, $V_L$ and the interchain linker (ICL) $(gly-gly-gly-gly-ser)_3$ fragments by overlap extension [Horton, R. M., et al., *Gene* 77:61–68 (1989)] followed by amplification with primers A and D. Specifically, equimolar amounts of the three fragments (40 ng each of $V_H$ and $V_L$ 10 ng of ICL) were combined in a 50 µl reaction containing 1× Vent reaction buffer (Promega), 0.2 mM dNTPs and 2 units Vent polymerase. The sample was denatured by heating at 94° C. for 5 minutes then the cycle (94° C. for 2 minutes followed by 72° C. for 4 minutes) was repeated seven times. Primers A and D were then added to a concentration of 0.5 µM and the cycle (94° C. for 2 minutes followed by 72° C. for 2 minutes) repeated 30 times. The reaction products were run on a 1 % low melting temperature gel and a 740 bp band corresponding to the assembled sFv fragment was excised. The complete sequence of the sFvTac gene was determined by the dideoxy chain termination method of Sanger [Sanger, F., et al., *Proc. Natl. Acad. Sci. USA* 74:5463–5467 (1977)].

3. Expression of the sFvTac gene in *E. coli*

The phagemid vector pHEN1 [Hoogenboom, H. R., et al., *Nucl. Acids Res.* 19:4133–4137 (1991)] was used for the production of the sFvTac in the non-suppressor *E. coli* strain HB2151. In this vector, the native anti-Tac heavy chain leader sequence is replaced by a signal sequence from the bacterial pelB gene and a c-myc peptide is added to the C-terminus for detection purposes. The pelB signal sequence directs the protein into the bacterial periplasm, allowing recovery of the sFv in semi-purified form by hypotonic shocking of the cells. For insertion into pHEN1, the assembled sFvTac gene was reamplified with primers D and G (Table 1), digested with NcoI and NotI and ligated into the vector pHEN1, which had been cut with NcoI and NotI. The resulting plasmid was designated pHENTac. For small scale production of the PelB/sFvTac fusion protein, a 25 ml culture of *E. coli* strain HB2151 containing pHENTac was grown to mid log phase in LB broth supplemented with ampicillin (100 µg/ml) and 0.1% glucose. IPTG was added to a concentration of 0.3 mM and the culture incubated for a further 3 hours at 37° C. Periplasmic extracts were then prepared by standard means.

4. Immunostaining of cells and FACS analysis

1×10⁶ Jurkat or C8166 cells were washed once in solution A (PBS, 1% fetal calf serum, 0.1% sodium azide) then incubated sequentially for 45 minutes on ice with (i) bacterial periplasmic extract diluted 1:10 in solution A, (ii) mAb 9E10, which recognizes the C-terminal myc peptide [Munroe, S. & Pelham, H., Cell 46:291–300 (1986)], (iii) FITC-conjugated goat anti-mouse IgG (Boehringer Manheim). The cells were washed twice with solution A between incubations and resuspended in PBS containing 4% formaldehyde for FACS analysis. Alternatively, steps (i) and (ii) were replaced by a single incubation with one of the following mAbs: anti-Tac for IL-2Rα, W6/32 for class I MHC (ATCC HB95), Leu-3a for CD4, Leu-5b for CD2, Leu-4 for CD3 (Beckton Dickinson), pan αβ for TCRαβ chains (Amac Inc., Maine).

5. Construction of mammalian cell expression vectors

For expression in mammalian cells, the assembled sFvTac gene was reamplified using primers A and H or A and I. The H primer introduces a stop codon at the end of $V_L$. The I primer introduces six additional amino acids (SEKDEL) at the C-terminus, followed by a stop codon. The amplified fragments were digested with HindIII and XbaI and ligated into the vector pRc/CMV (Invitrogen). The resulting plasmids, designated pCMVTac and pCMVTacKDEL, contain the sFvTac gene under the control of the cytomegalovirus immediate early promoter and a neo gene, conferring resistance to G418.

6. Transfections and cell cloning pCMVTac and pCMVTacKDEL were linearized at an XmnI site within the β-lactamase gene and introduced into Jurkat cells by electroporation. 1×10⁷ cells were pulsed with 10 μg of DNA (300 V, 960 μF) using a Gene Pulser (Biorad). G418 selection was applied at 0.8 mg/ml after 36 hours. Two weeks later, G418 resistant cells were seeded at 0.3 cell per well in 96-well plates using 25% conditioned medium.

7. Metabolic labelling of cells and immunoprecipitation

5×10⁶ C8166 cells or 1×10⁷ Jurkat cells stimulated for 6–8 hours with PHA (1 μg/ml) and PMA (50 ng/ml) were washed once in PBS and incubated for 12 hours in 5 ml cysteine-free RPMI-1640 containing 10% fetal calf serum, antibiotics and 100 μCi ³⁵S cysteine (Dupont NEN). The labelled cells were washed with PBS and solubilized in 1 ml RIPA buffer (0.15M NaCl, 0.05M Tris.HCl pH7.2, 1% Triton X-100, 0.1% SDS, 1% sodium deoxycholate) for 20 minutes on ice. Lysates were clarified by centrifugation at 33 krpm for 1 hour at 4° C. IL-2Rα was immunoprecipitated by incubation of lysates with mAb 7G7/B6 coupled to protein A-sepharose beads (Pharmacia) for 12–18 hours at 4° C. The single-chain antibodies were immunoprecipitated using polyclonal rabbit anti-mouse IgG (Sigma) attached to protein A sepharose beads. Samples were washed five times with RIPA buffer and analyzed by SDS-PAGE (10% gels). Gels were fixed and treated with Enhance (Dupont NEN) prior to autoradiography.

8. Pulse-chase analysis

Jurkat cells were stimulated for 12 hours with PHA and PMA then washed in PBS and incubated at 5×10⁶ per ml for 2.5 hours in cysteine-free medium. ³⁵S-cysteine was then added at 100 μCi/ml (0.2 mM). 30 minutes later, cells were diluted five-fold with complete medium supplemented with 2 mM cold L-cystine. 4×10⁶ cells were harvested at timed intervals and processed for immunoprecipitation as described above.

9. Endoglycosidase H treatment

IL-2Rα immunoprecipitated from Jurkat cells using mAb 7G7/B6 was eluted from the protein A-sepharose beads by boiling for 3 minutes in 2× Endo H digestion buffer (100 mM sodium citrate pH5.5, 1% SDS, 5% 2-mercaptoethanol). An equal volume of distilled water was then added and the sample incubated for 3 hours at 37° C. in the presence or absence of 0.05 units/ml Endoglycosidase H (Boehringer Manheim).

10. Results

A. Construction of sFvTac, a single chain antibody against IL-2Rα

A single-chain variable region fragment of the anti-Tac mAb was constructed as outlined in FIG. 1. Briefly, the heavy and light chain variable regions of anti-Tac mRNA were amplified from the HD245-332 hybridoma by RT-PCR and assembled into a single chain Fv gene by overlap extension. The sFvTac protein was first synthesized in *E. coli* and shown by flow cytometry to bind specifically to a cell line (C8166) which expresses high levels of IL-2Rα (data not shown). A control sFv directed against the human immunodeficiency virus type 1 Tat protein did not bind to the C8166 cells and neither sFv bound to the Jurkat cell line, which does not express IL-2Rα unless stimulated.

Figure 2:
FIG. 2 is an autoradiogram showing pulse chase analysis of the single chain antibodies sFvTac and sFvTacKDEL in stably transfected Jurkat cells. A 40 kD protein coprecipitates only with sFvTac.
Figure 3A:
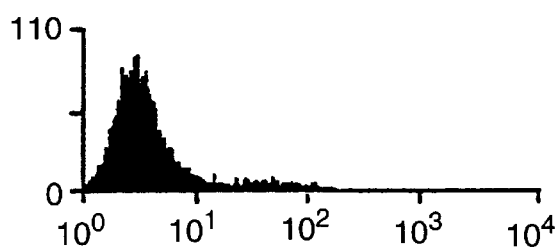
FIGS. 3A–D shows the FACS analysis of IL-2Rα expression in Jurkat clones.
Figure 3B:
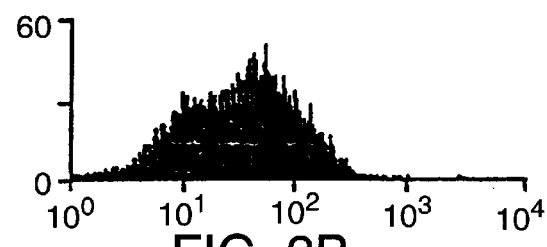
Figure 3C:
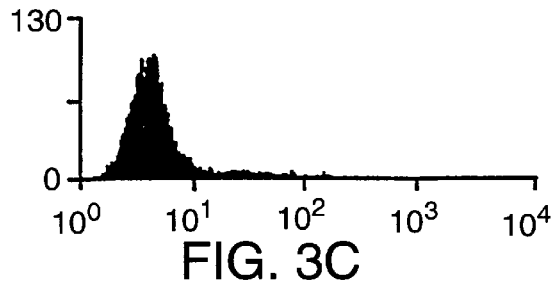
Figure 3D:
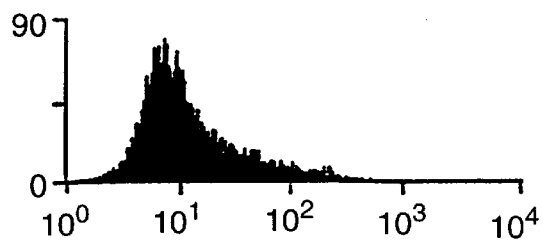

B. Stable expression and intracellular retention of ER and non ER forms of sFvTac Two versions of the sFvTac gene, differing only in the presence or absence of a C-terminal ER-retention signal (amino acids KDEL), were stably transfected into Jurkat cells and single cell clones were generated. Both versions contain the native $V_H$ leader peptide, to direct the protein into the endoplasmic reticulum. Pulse chase analysis revealed the sFv molecules to be extremely stable, exhibiting intracellular half-lives of 4–6 hours for sFvTac and >30 h for sFvTacKDEL (FIG. 2). Only trace amounts of antibody were detectable in the culture supernatants, indicating that neither sFv is secreted to a significant extent. The basis for intracellular retention of the sFvTac antibody without KDEL is not clear but the same phenomenon has been noted with other sFv molecules [Marasco, W. A., et al., *Proc. Natl. Acad. Sci. USA* 90:7889–7893 (1993) and references cited therein].

C. Intracellular expression of sFvTac and sFvTacKDEL inhibits cell surface expression of IL-2Rα

The ability of sFvTac intrabodies to downregulate IL-2Rα was assessed using Jurkat cells, which do not express IL-2Rα under normal circumstances but can be induced to do so by treatment with phorbol ester and/or stimulation via the T cell receptor [Greene, W. C., et al., *J. Immunol.* 133:1042–1047 (1984)]. See FIG. 3. In this and other respects, the regulation of IL-2Rα in Jurkat cells mimics that seen in peripheral blood T cells. IL-2Rα expression in the transfected Jurkat clones was assessed by FACS analysis after 18 hour treatment with PHA and PMA. 16/16 independent clones expressing the ER antibody sFvTacKDEL showed complete inhibition of IL-2Rα induction, consistent with a block to the cell surface transport of IL-Rα in these cells (FIG. 3, panel C). 3/15 clones expressing sFvTac also show downregulation of the α chain but this was incomplete, as evidenced by breakthrough expression of IL-2Rα at the cell surface (panel D). The remaining 12 sFvTac clones show normal levels of IL-2Rα after PHA/PMA treatment. In each of these 12 clones, an unidentified 40 kD cellular protein was found to coprecipitate with sFvTac and may interfere with the formation of sFv/IL-2Rα complexes (FIG. 4, lane 5). The 40 kD protein was present in unstimulated Jurkat cells, had a 90 minute half life and was not recognized by mAb 7G7/B6 (FIG. 1 and data not shown). In spite of its similar size, the interfering protein is unlikely therefore be the 40 kD precursor of IL-2Rα.

To determine whether the IL-2Rα downregulation observed in all sFvTacKDEL and some sFvTac clones was specific for IL-2Rα, the cell surface expression of other plasma membrane proteins was examined. The results show that the transport of MHC class I, the T cell antigen receptor (TCR), CD2, CD3 and CD4 was unaffected by the intracellular expression of sFvTac or sFvTacKDEL (FIG. 5). We note that expression of the TCR/CD3 complex was heterogeneous in the parent Jurkat cell population and variable in the single cell subclones. As TCR and CD3 chains can only be transported to the cell surface as a preassembled complex, the tight linkage of the CD3 and TCR expression was expected.

Figure 7:
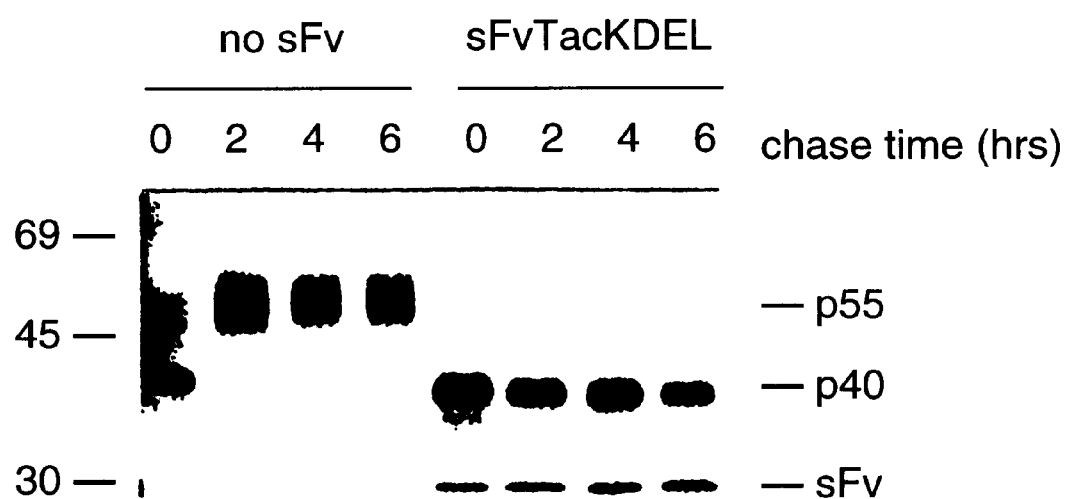
FIG. 7 is an autoradiogram showing a pulse chase analysis of IL-2Rα in control Jurkat cells and Jurkat cells expressing sFvTacKDEL.

D. IL-2Rα is retained as an endo H-sensitive precursor in cells expressing sFvTacKDEL In common with most secreted and cell surface proteins, newly synthesized IL-2Rα undergoes extensive post-translational processing in the ER and golgi. The protein has 2 potential N-linked glycosylation sites and carbohydrate accounts for almost half of the molecular mass of the mature receptor chain. SDS-PAGE analysis of IL-2Rα immunoprecipitated from C8166 or PHA/PMA-treated Jurkat cells revealed 2 forms: a predominant 55 kD form (p55), representing the mature receptor, and a less abundant 40 kD form (p40) which has previously been identified as a an immature form of IL-2Rα. [Wano, Y., et al. *J. Immunol.* 132:3005–3010 (1984)]. FIG. 6, lane 1. Pulse chase experiments confirmed the 40 kD protein to be a natural precursor of p55, which is chased into the higher molecular weight form within two hours in control Jurkat cells. FIG. 7. PHA/PMA treatment of Jurkat cells expressing sFvTacKDEL was associated with intracellular accumulation of the p40 precursor and the complete absence of p55 (FIG. 6, lane 3 and 4*b*). Moreover, a 30 kD protein identical in size to the single-chain antibody coprecipitated with p40 IL-2Rα in these cells (FIGS. 6 and 7). The p40 form of IL-2Rα was sensitive to endoglycosidase H digestion and is therefore a high mannose glycoprotein (FIG. 6 lanes 1–4). The absence of complex oligosaccharides, which are added in the medial golgi and render the glycoprotein resistant to endo-H, suggests that p40 is located in a pre-golgi or early golgi compartment. As expected, both the mature p55 (FIG. 6, lanes 1 and 2) and soluble Tac a form of IL-2Rα that is shed into the extracellular fluid, (not shown) were insensitive to endo H digestion. These results indicate that IL-2Rα is translocated into the ER and core glycosylated in cells expressing sFvTacKDEL, but is unable to proceed to the golgi owing to its stable association with the ER-localized intrabody.

E. Rapid degradation of IL-2Rα in cells expressing SfVTac

In sFvTac clones which show downregulation of IL-2Rα, very little IL-2Rα (either p55 or p40) could be detected by immunoprecipitation in the cell lysates, suggesting rapid degradation of these antibody/IL-2Rα complexes (FIG. 6, lanes 5 and 6). This is in marked contrast to the apparently stable complexes formed with sFvTacKDEL and indicates that the presence or absence of an ER retention signal on the antibody can profoundly influence the fate of intracellular immune complexes.

TABLE 3

Primers used for construction of the sFvTac and sFvTac KDEL genes. Translation start and stop codons in primers A, H and I are underscored. In degenerate primer mixers (B and C), nucleotide alternatives are shown in parentheses.

| Primer | Description | Sequence | | Restriction Site |
|---|---|---|---|---|
| A | Forward V$_H$ | 5'TTTAAGCTTACC<u>ATG</u>GAAAGGCACTG GATC3' | (SEQ ID NO:49) | HindIII |
| B | Reverse J$_H$ | 5'TG(A/C)GGAGACGGTGACC(A/G) (A/T)GGTCCCT3' | (SEQ ID NO:50) | BstEII |
| C | Forward V$_K$ | 5'GAGCTCGTGCTCAC(C/A)CA(G/A) (T/A)CTCCA3' | (SEQ ID NO:51) | SacI |
| D | Reverse C$_K$ | 5'ATTTGCGGCCGCTACAGTTGGTGCAG CATC3' | (SEQ ID NO:52) | NotI |
| E | Forward J$_H$ | 5'GGGACCTCGGTCACCGTCTCCTCA3' | (SEQ ID NO:53) | BstEII |
| F | Reverse V$_K$ | 5'TGGAGACTGGGTGAGCACGAGCTCAG ATCC3' | (SEQ ID NO:54) | SacI |
| G | Forward V$_H$ FR1 | 5'TTTACCATGGCCGAGGTTCAGCTGCA GCAGTCTGGG3' | (SEQ ID NO:55) | NcoI |
| H | Reverse C$_k$-stop | 5'GGGTCTAGACTCGAGGATCC<u>TTATTA</u> TACAGTTGGTGCAGCATC3' | (SEQ ID NO:56) | XbaI |
| I | Reverse C$_{k\text{-KDEL-stop}}$ | 5'TTTTCTAGA<u>ATTATTA</u>CAGCTCGTCCTT TTCGCTTACAGTTGGTGCAGCATC3' | (SEQ ID NO:57) | XbaI |

What is claimed:

1. A vector for the intracellular binding of an endogenous protein that traverses a cellular membrane, referred to as a target antigen, which comprises:
a nucleic acid segment encoding a variable heavy chain sequence of an antibody which selectively binds to said target antigen and said antibody's corresponding variable light chain sequence operably linked to a promoter, wherein said nucleic acid sequence does not encode said antibody's wild-type leader sequence for the variable chains and said antibody's secretory sequences,
thereby adapting said antibody expressed by said nucleic acid sequence for intracellular binding to said target antigen.

2. The vector of claim 1, wherein the target antigen is an IL-2 receptor or a component of an IL-2 receptor.

3. The vector of claim 2, wherein the antibody is an antibody that binds to the IL2Rα chain.

4. The vector of claim 3, wherein the target antigen is IL-2Rα.

5. The vector of claim 2, wherein the antibody gene further encodes an intracellular localization sequence to the endoplasmic reticulum.

6. The vector of claim 1, wherein the antibody gene further encodes an intracellular localization sequence.

7. A pharmaceutical composition comprising the vector system of claim 1 together with a pharmaceutically acceptable carrier thereof.

8. The vector of claim 1 wherein the protein that traverses the cellular membrane is selected from the group of proteins consisting of a transmembrane protein, an integral membrane protein, a secreted protein and a gp1-anchored protein.

9. The vector of claim 8 wherein said protein is a transmembrane protein.

10. A DNA vector comprising a gene encoding an antibody that binds to an IL2Rα operably linked to a promoter, wherein the antibody gene does not encode a secretory signal sequence.

11. The DNA vector of claim 10, wherein the gene comprises a $V_H$-coding DNA sequence, a linker coding DNA sequence, and a $V_L$-coding DNA sequence, encoding a single chain variable fragment, and contains an intracellular localization sequence.

12. The DNA vector of claim 11, wherein the localization sequence is specific to the endoplasmic reticulum, said sequence is selected from the group consisting of SEQ ID NO:17, SEQ ID NO:18, SEQ ID NO:19, SEQ ID NO:21 AND SEQ ID NO:22.

13. A vector for the intracellular binding of an endogenous protein that traverses a cellular membrane, referred to as a target antigen, which comprises:

a nucleic acid segment encoding a variable heavy chain sequence of an antibody which selectively binds to said target antigen and said antibody's corresponding variable light chain sequence operably linked to a promoter, wherein said nucleic acid sequence also encodes an endoplasmic reticulum or golgi apparatus localization sequence, thereby adapting said antibody expressed by said nucleic acid sequence to be retained in the endoplasmic reticulum-golgi apparatus for intracellular binding to said target antigen.

14. The vector of claim 13, wherein the antibody contains a leader sequence.

15. The vector of claim 13, wherein the target antigen is a cellular receptor or a component of a cellular receptor.

16. The vector of claim 13, wherein the target antigen is an IL-2 receptor or a component or an IL-2 receptor.

17. The vector of claim 13 wherein the target antigen is IL-2Rα.

18. A method for the intracellular binding of a protein that traverses a cellular membrane, referred to as a target antigen, which comprises:

(a) delivery of a nucleic acid segment containing a promoter operably linked to a gene encoding an antibody that binds to said target antigen, wherein the antibody expressed by said gene does not have said antibody's secretory sequences or any substitution for said secretory sequences;

(b) intracellular expression of said antibody in a form that binds to said target antigen; and (c) intracellular binding of said target antigen by said antibody.

19. A method for the intracellular binding of a protein that traverses a cellular membrane, referred to as a target antigen, which comprises:

(a) delivery of a nucleic acid segment containing a promoter operably linked to an antibody gene encoding an antibody that binds to said target antigen, wherein the nucleic acid segment also encodes an endoplasmic reticulum or golgi apparatus localization sequence;

(b) intracellular expression of said antibody in a form that binds to said target antigen;

(c) localization of said antibody in said cell's endoplasmic reticulum golgi apparatus; and (d) intracellular binding of said target antigen by said antibody.

20. The method of claim 19, wherein the target antigen is a cellular receptor or a component of a cellular receptor.

21. The method of claim 20, wherein the target antigen is an IL-2 receptor or a component of an IL-2 receptor.

22. The method of claim 21, wherein the target antigen is IL-2Rα.

23. The method of claim 19, wherein the antibody is an antibody that binds to an IL2 receptor or a component of an IL-2 receptor.

24. The method of claim 23, wherein the antibody gene further encodes an intracellular localization sequence.

25. The method of claim 23, wherein multiple target antigens are intracellularly bound by multiple antibodies.

26. The method of claim 19, wherein the antibody is that binds to IL2Rα or IL-2Rβ.

27. The method of claim 26, wherein the antibody is that binds to IL-2Rα.

28. The method of claim 19, wherein said endoplasmic reticulum or golgi apparatus retention localization sequence is an endoplasmic reticulum localization sequence.

29. The method of claim 28, therein said endoplasmic reticulum localization sequence is KDEL (SEQ. ID No. 17).

30. The method of claim 19, wherein the antibody contains a leader sequence.

31. The method of claim 19, wherein the target antigen is a transmembrane growth factor.

32. The method of claim 31, wherein the transmembrane protein is selected from the group consisting of erb, neu, fms, ros and kit.

* * * * *

SEQUENCE LISTING (1) GENERAL INFORMATION:

(iii) NUMBER OF SEQUENCES: 58

(2) INFORMATION FOR SEQ ID NO:1:

(i) SEQUENCE CHARACTERISTICS:
           (A) LENGTH: 15 amino acids
           (B) TYPE: amino acid
           (D) TOPOLOGY: linear (xi) SEQUENCE DESCRIPTION: SEQ ID NO:1:

Gly Gly Gly Gly Ser Gly Gly Gly Gly Ser Gly Gly Gly Gly Ser
1               5                  10                  15

(2) INFORMATION FOR SEQ ID NO:2:

(i) SEQUENCE CHARACTERISTICS:
           (A) LENGTH: 15 amino acids
           (B) TYPE: amino acid
           (D) TOPOLOGY: linear (xi) SEQUENCE DESCRIPTION: SEQ ID NO:2:

Glu Ser Gly Arg Ser Gly Gly Gly Gly Ser Gly Gly Gly Gly Ser
1               5                  10                  15

(2) INFORMATION FOR SEQ ID NO:3:

(i) SEQUENCE CHARACTERISTICS:
           (A) LENGTH: 14 amino acids
           (B) TYPE: amino acid
           (D) TOPOLOGY: linear (xi) SEQUENCE DESCRIPTION: SEQ ID NO:3:

Glu Gly Lys Ser Ser Gly Ser Gly Ser Glu Ser Lys Ser Thr
1               5                  10

(2) INFORMATION FOR SEQ ID NO:4:

(i) SEQUENCE CHARACTERISTICS:
           (A) LENGTH: 15 amino acids
           (B) TYPE: amino acid
           (D) TOPOLOGY: linear (xi) SEQUENCE DESCRIPTION: SEQ ID NO:4:

Glu Gly Lys Ser Ser Gly Ser Gly Ser Glu Ser Lys Ser Thr Gln
1               5                  10                  15

(2) INFORMATION FOR SEQ ID NO:5:

(i) SEQUENCE CHARACTERISTICS:
           (A) LENGTH: 14 amino acids
           (B) TYPE: amino acid
           (D) TOPOLOGY: linear (xi) SEQUENCE DESCRIPTION: SEQ ID NO:5:

Glu Gly Lys Ser Ser Gly Ser Gly Ser Glu Ser Lys Val Asp
1               5                  10

(2) INFORMATION FOR SEQ ID NO:6:

(i) SEQUENCE CHARACTERISTICS:
           (A) LENGTH: 14 amino acids
           (B) TYPE: amino acid
           (D) TOPOLOGY: linear (xi) SEQUENCE DESCRIPTION: SEQ ID NO:6:

Gly Ser Thr Ser Gly Ser Gly Lys Ser Ser Glu Gly Lys Gly
1               5                   10

(2) INFORMATION FOR SEQ ID NO:7:

(i) SEQUENCE CHARACTERISTICS:
            (A) LENGTH: 18 amino acids
            (B) TYPE: amino acid
            (D) TOPOLOGY: linear (xi) SEQUENCE DESCRIPTION: SEQ ID NO:7:

Lys Glu Ser Gly Ser Val Ser Ser Glu Gln Leu Ala Gln Phe Arg Ser
1               5                   10                  15

Leu Asp (2) INFORMATION FOR SEQ ID NO:8:

(i) SEQUENCE CHARACTERISTICS:
            (A) LENGTH: 16 amino acids
            (B) TYPE: amino acid
            (D) TOPOLOGY: linear (xi) SEQUENCE DESCRIPTION: SEQ ID NO:8:

Glu Ser Gly Ser Val Ser Ser Glu Glu Leu Ala Phe Arg Ser Leu Asp
1               5                   10                  15

(2) INFORMATION FOR SEQ ID NO:9:

(i) SEQUENCE CHARACTERISTICS:
            (A) LENGTH: 35 base pairs
            (B) TYPE: nucleic acid
            (C) STRANDEDNESS: single
            (D) TOPOLOGY: linear (xi) SEQUENCE DESCRIPTION: SEQ ID NO:9:

TTTGCGGCCG CTCAGGTGCA RCTGCTCGAG                                30

TCYGG                                                           35

(2) INFORMATION FOR SEQ ID NO:10:

(i) SEQUENCE CHARACTERISTICS:
            (A) LENGTH: 66 base pairs
            (B) TYPE: nucleic acid
            (C) STRANDEDNESS: single
            (D) TOPOLOGY: linear (xi) SEQUENCE DESCRIPTION: SEQ ID NO:10:

AGATCCGCCG CCACCGCTCC CACCACCTCC                                30

GGAGCCACCG CCACCTGAGG TGACCGTGAC                                60

CRKGGT                                                          66

(2) INFORMATION FOR SEQ ID NO:11:

(i) SEQUENCE CHARACTERISTICS:
            (A) LENGTH: 69 base pairs
            (B) TYPE: nucleic acid
            (C) STRANDEDNESS: single
            (D) TOPOLOGY: linear (xi) SEQUENCE DESCRIPTION: SEQ ID NO:11:

GGTGGCGGTG GCTCCGGAGG TGGTGGGAG                                 29

CGGTGGCGGC GGATCTGAGC TCSWGMTGACC                               60

CAGTCTCCA                                                              69

(2) INFORMATION FOR SEQ ID NO:12:

(i) SEQUENCE CHARACTERISTICS:
        (A) LENGTH: 47 base pairs
        (B) TYPE: nucleic acid
        (C) STRANDEDNESS: single
        (D) TOPOLOGY: linear (xi) SEQUENCE DESCRIPTION: SEQ ID NO:12:

GGGTCTAGAC TCGAGGATCC TTATTAACGC                                       30

GTTGGTGCAG CCACAGT                                                     47

(2) INFORMATION FOR SEQ ID NO:13:

(i) SEQUENCE CHARACTERISTICS:
        (A) LENGTH: 6 amino acids
        (B) TYPE: amino acid
        (D) TOPOLOGY: linear (xi) SEQUENCE DESCRIPTION: SEQ ID NO:13:

Ser Glu Lys Asp Glu Leu
1               5

(2) INFORMATION FOR SEQ ID NO:14:

(i) SEQUENCE CHARACTERISTICS:
        (A) LENGTH: 59 base pairs
        (B) TYPE: nucleic acid
        (C) STRANDEDNESS: single
        (D) TOPOLOGY: linear (xi) SEQUENCE DESCRIPTION: SEQ ID NO:14:

GGGTCTAGAC TCGAGGATCC TTATTACAGC                                       30

TCGTCCTTTT CGCTTGGTGC AGCCACAGT                                        59

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

TTTACCATGG AACATCTGTG GTTC                                             24

(2) INFORMATION FOR SEQ ID NO:16:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (xi) SEQUENCE DESCRIPTION: SEQ ID NO:16:

TTAGCGCGCT GAGGTGACCG TGACCRKGGT                                       30

(2) INFORMATION FOR SEQ ID NO:17:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:17:

```
Lys Asp Glu Leu
 1

(2) INFORMATION FOR SEQ ID NO:18:

(i) SEQUENCE CHARACTERISTICS:
         (A) LENGTH: 4 amino acids
         (B) TYPE: amino acid
         (D) TOPOLOGY: linear (xi) SEQUENCE DESCRIPTION: SEQ ID NO:18:

Asp Asp Glu Leu
 1

(2) INFORMATION FOR SEQ ID NO:19:

(i) SEQUENCE CHARACTERISTICS:
         (A) LENGTH: 4 amino acids
         (B) TYPE: amino acid
         (D) TOPOLOGY: linear (xi) SEQUENCE DESCRIPTION: SEQ ID NO:19:

Asp Glu Glu Leu
 1

(2) INFORMATION FOR SEQ ID NO:20:

(i) SEQUENCE CHARACTERISTICS:
         (A) LENGTH: 4 amino acids
         (B) TYPE: amino acid
         (D) TOPOLOGY: linear (xi) SEQUENCE DESCRIPTION: SEQ ID NO:20:

Gln Glu Asp Leu
 1

(2) INFORMATION FOR SEQ ID NO:21:

(i) SEQUENCE CHARACTERISTICS:
         (A) LENGTH: 4 amino acids
         (B) TYPE: amino acid
         (D) TOPOLOGY: linear (xi) SEQUENCE DESCRIPTION: SEQ ID NO:21:

Arg Asp Glu Leu
 1

(2) INFORMATION FOR SEQ ID NO:22:

(i) SEQUENCE CHARACTERISTICS:
         (A) LENGTH: 7 amino acids
         (B) TYPE: amino acid
         (D) TOPOLOGY: linear (xi) SEQUENCE DESCRIPTION: SEQ ID NO:22:

Pro Lys Lys Lys Arg Lys Val
 1               5

(2) INFORMATION FOR SEQ ID NO:23:

(i) SEQUENCE CHARACTERISTICS:
         (A) LENGTH: 7 amino acids
         (B) TYPE: amino acid
         (D) TOPOLOGY: linear (xi) SEQUENCE DESCRIPTION: SEQ ID NO:23:

Pro Gln Lys Lys Ile Lys Ser
```

```
1               5
```

(2) INFORMATION FOR SEQ ID NO:24:

(i) SEQUENCE CHARACTERISTICS:
        (A) LENGTH: 5 amino acids
        (B) TYPE: amino acid
        (D) TOPOLOGY: linear (xi) SEQUENCE DESCRIPTION: SEQ ID NO:24:

```
Gln Pro Lys Lys Pro
1               5
```

(2) INFORMATION FOR SEQ ID NO:25:

(i) SEQUENCE CHARACTERISTICS:
        (A) LENGTH: 12 amino acids
        (B) TYPE: amino acid
        (D) TOPOLOGY: linear (xi) SEQUENCE DESCRIPTION: SEQ ID NO:25:

```
Arg Lys Lys Arg Arg Gln Arg Arg Arg Ala His Gln
1               5                   10
```

(2) INFORMATION FOR SEQ ID NO:26:

(i) SEQUENCE CHARACTERISTICS:
        (A) LENGTH: 16 amino acids
        (B) TYPE: amino acid
        (D) TOPOLOGY: linear (xi) SEQUENCE DESCRIPTION: SEQ ID NO:26:

```
Arg Gln Ala Arg Arg Asn Arg Arg Arg Trp Arg Glu Arg Gln Arg
1               5                   10                  15
```

(2) INFORMATION FOR SEQ ID NO:27:

(i) SEQUENCE CHARACTERISTICS:
        (A) LENGTH: 19 amino acids
        (B) TYPE: amino acid
        (D) TOPOLOGY: linear (xi) SEQUENCE DESCRIPTION: SEQ ID NO:27:

```
Met Pro Leu Thr Arg Arg Arg Pro Ala Ala Ser Gln Ala Leu Ala Pro
1               5                   10                  15

Pro Thr Pro
```

(2) INFORMATION FOR SEQ ID NO:28:

(i) SEQUENCE CHARACTERISTICS:
        (A) LENGTH: 15 amino acids
        (B) TYPE: amino acid
        (D) TOPOLOGY: linear (xi) SEQUENCE DESCRIPTION: SEQ ID NO:28:

```
Met Asp Asp Gln Arg Asp Leu Ile Ser Asn Asn Glu Gln Leu Pro
1               5                   10                  15
```

(2) INFORMATION FOR SEQ ID NO:29:

(i) SEQUENCE CHARACTERISTICS:
        (A) LENGTH: 32 amino acids
        (B) TYPE: amino acid
        (D) TOPOLOGY: linear (xi) SEQUENCE DESCRIPTION: SEQ ID NO:29:

```
Met Leu Phe Asn Leu Arg Xaa Xaa Leu Asn Asn Ala Ala Phe Arg His
```

```
         1               5                  10                 15
Gly His Asn Phe Met Val Arg Asn Phe Arg Cys Gly Gln Pro Leu Xaa
                20                  25                  30
```

(2) INFORMATION FOR SEQ ID NO:30:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:30:

```
Gly Cys Val Cys Ser Ser Asn Pro
1               5
```

(2) INFORMATION FOR SEQ ID NO:31:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:31:

```
Gly Gln Thr Val Thr Thr Pro Leu
1               5
```

(2) INFORMATION FOR SEQ ID NO:32:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:32:

```
Gly Gln Glu Leu Ser Gln His Glu
1               5
```

(2) INFORMATION FOR SEQ ID NO:33:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:33:

```
Gly Asn Ser Pro Ser Tyr Asn Pro
1               5
```

(2) INFORMATION FOR SEQ ID NO:34:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:34:

```
Gly Val Ser Gly Ser Lys Gly Gln
1               5
```

(2) INFORMATION FOR SEQ ID NO:35:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:35:

```
Gly Gln Thr Ile Thr Thr Pro Leu
1               5
```

(2) INFORMATION FOR SEQ ID NO:36:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:36:

```
Gly Gln Thr Ile Thr Thr Pro Leu
1               5
```

(2) INFORMATION FOR SEQ ID NO:37:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:37:

```
Gly Gln Ile Phe Ser Arg Ser Ala
1               5
```

(2) INFORMATION FOR SEQ ID NO:38:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:38:

```
Gly Gln Ile His Gly Leu Ser Pro
1               5
```

(2) INFORMATION FOR SEQ ID NO:39:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:39:

```
Gly Ala Arg Ala Ser Val Leu Ser
1               5
```

(2) INFORMATION FOR SEQ ID NO:40:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:40:

```
Gly Cys Thr Leu Ser Ala Glu Glu
1               5
```

(2) INFORMATION FOR SEQ ID NO:41:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:41:

```
Gly Gln Asn Leu Ser Thr Ser Asn
1               5
```

(2) INFORMATION FOR SEQ ID NO:42:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:42:

```
Gly Ala Ala Leu Thr Ile Leu Val
1               5
```

(2) INFORMATION FOR SEQ ID NO:43:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:43:

```
Gly Ala Ala Leu Thr Leu Leu Gly
1               5
```

(2) INFORMATION FOR SEQ ID NO:44:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:44:

```
Gly Ala Gln Val Ser Ser Gln Lys
1               5
```

(2) INFORMATION FOR SEQ ID NO:45:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:45:

```
Gly Ala Gln Leu Ser Arg Asn Thr
1               5
```

(2) INFORMATION FOR SEQ ID NO:46:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:46:

```
Gly Asn Ala Ala Ala Ala Lys Lys
1               5
```

(2) INFORMATION FOR SEQ ID NO:47:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:47:

```
Gly Asn Glu Ala Ser Tyr Pro Leu
1               5
```

(2) INFORMATION FOR SEQ ID NO:48:

(i) SEQUENCE CHARACTERISTICS:
        (A) LENGTH: 8 amino acids
        (B) TYPE: amino acid
        (D) TOPOLOGY: linear (xi) SEQUENCE DESCRIPTION: SEQ ID NO:48:

Gly Ser Ser Lys Ser Lys Pro Lys
1               5

(2) INFORMATION FOR SEQ ID NO:49:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO:49:

TTTAAGCTTA CCATGGAAAG GCACTGGATC                                    30

(2) INFORMATION FOR SEQ ID NO:50:

(i) SEQUENCE CHARACTERISTICS:
        (A) LENGTH: 25 base pairs
        (B) TYPE: nucleic acid
        (C) STRANDEDNESS: unknown
        (D) TOPOLOGY: unknown (xi) SEQUENCE DESCRIPTION: SEQ ID NO:50:

TGMGGAGACG GTGACCRWGG TCCCT                                         25

(2) INFORMATION FOR SEQ ID NO:51:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (xi) SEQUENCE DESCRIPTION: SEQ ID NO:51:

GAGCTCGTGC TCACMCARWC TCCA                                          24

(2) INFORMATION FOR SEQ ID NO:52:

(i) SEQUENCE CHARACTERISTICS:
        (A) LENGTH: 30 base pairs
        (B) TYPE: nucleic acid
        (C) STRANDEDNESS: unknown
        (D) TOPOLOGY: unknown (xi) SEQUENCE DESCRIPTION: SEQ ID NO:52:

ATTTGCGGCC GCTACAGTTG GTGCAGCATC                                    30

(2) INFORMATION FOR SEQ ID NO:53:

(i) SEQUENCE CHARACTERISTICS:
        (A) LENGTH: 24 base pairs
        (B) TYPE: nucleic acid
        (C) STRANDEDNESS: unknown
        (D) TOPOLOGY: unknown (xi) SEQUENCE DESCRIPTION: SEQ ID NO:53:

GGGACCTCGG TCACCGTCTC CTCA                                          24

(2) INFORMATION FOR SEQ ID NO:54:

-continued (i) SEQUENCE CHARACTERISTICS:
    (A) LENGTH: 30 base pairs
    (B) TYPE: nucleic acid
    (C) STRANDEDNESS: unknown
    (D) TOPOLOGY: unknown (xi) SEQUENCE DESCRIPTION: SEQ ID NO:54:

TGGAGACTGG GTGAGCACGA GCTCAGATCC                                    30

(2) INFORMATION FOR SEQ ID NO:55:

(i) SEQUENCE CHARACTERISTICS:
        (A) LENGTH: 36 base pairs
        (B) TYPE: nucleic acid
        (C) STRANDEDNESS: unknown
        (D) TOPOLOGY: unknown (xi) SEQUENCE DESCRIPTION: SEQ ID NO:55:

TTTACCATGG CCGAGGTTCA GCTGCAGCAG TCTGGG                              36

(2) INFORMATION FOR SEQ ID NO:56:

(i) SEQUENCE CHARACTERISTICS:
        (A) LENGTH: 44 base pairs
        (B) TYPE: nucleic acid
        (C) STRANDEDNESS: unknown
        (D) TOPOLOGY: unknown (xi) SEQUENCE DESCRIPTION: SEQ ID NO:56:

GGGTCTAGAC TCGAGGATCC TTATTATACA GTTGGTGCAG CATC                     44

(2) INFORMATION FOR SEQ ID NO:57:

(i) SEQUENCE CHARACTERISTICS:
        (A) LENGTH: 51 base pairs
        (B) TYPE: nucleic acid
        (C) STRANDEDNESS: unknown
        (D) TOPOLOGY: unknown (xi) SEQUENCE DESCRIPTION: SEQ ID NO:57:

TTTTCTAGAT TATTACAGCT CGTCCTTTTC GCTTACAGTT GGTGCAGCAT C              51

(2) INFORMATION FOR SEQ ID NO:58:

(i) SEQUENCE CHARACTERISTICS:
        (A) LENGTH: 4 amino acids
        (B) TYPE: amino acid
        (D) TOPOLOGY: linear (xi) SEQUENCE DESCRIPTION: SEQ ID NO:58:

Arg Lys Lys Arg